US011154510B2

(12) United States Patent
Albayrak

(10) Patent No.: US 11,154,510 B2
(45) Date of Patent: *Oct. 26, 2021

(54) PROCESS FOR THE PREPARATION OF DRUG LOADED MICROPARTICLES

(71) Applicant: Alrise Biosystems GmbH, Berlin (DE)

(72) Inventor: Celal Albayrak, Berlin (DE)

(73) Assignee: Alrise Biosystems GmbH, Berlin (DE)

( * ) Notice: Subject to any disclaimer, the term of this patent is extended or adjusted under 35 U.S.C. 154(b) by 156 days.

This patent is subject to a terminal disclaimer.

(21) Appl. No.: 15/735,127

(22) PCT Filed: Jun. 11, 2015

(86) PCT No.: PCT/EP2015/063061
§ 371 (c)(1),
(2) Date: Dec. 8, 2017

(87) PCT Pub. No.: WO2016/198113
PCT Pub. Date: Dec. 15, 2016

(65) Prior Publication Data
US 2020/0030245 A1 Jan. 30, 2020

(51) Int. Cl.
A61K 9/51 (2006.01)
A61K 9/00 (2006.01)
A61K 9/16 (2006.01)
A61K 9/50 (2006.01)
A61K 31/519 (2006.01)
B82Y 5/00 (2011.01)

(52) U.S. Cl.
CPC .......... *A61K 9/5153* (2013.01); *A61K 9/0019* (2013.01); *A61K 9/1647* (2013.01); *A61K 9/1694* (2013.01); *A61K 9/5031* (2013.01); *A61K 9/5089* (2013.01); *A61K 9/5192* (2013.01); *A61K 31/519* (2013.01); *B82Y 5/00* (2013.01)

(58) Field of Classification Search
CPC .. A61K 9/5153; A61K 9/1647; A61K 9/5031; A61K 9/1694; A61K 9/1682; A61K 9/5089; A61K 9/5192
See application file for complete search history.

(56) References Cited

U.S. PATENT DOCUMENTS

| | | | |
|---|---|---|---|
| 4,145,434 A | 3/1979 | van der Burg | |
| 5,102,668 A | 4/1992 | Eichel et al. | |
| 5,650,173 A | 7/1997 | Ramstack et al. | |
| 5,792,477 A | 8/1998 | Rickey et al. | |
| 2003/0133357 A1* | 7/2003 | Lyons | A61K 9/1647 366/336 |
| 2005/0069591 A1 | 3/2005 | Bernstein et al. | |
| 2006/0084692 A1 | 4/2006 | Wong et al. | |
| 2010/0130478 A1 | 5/2010 | Moses et al. | |
| 2011/0166194 A1 | 7/2011 | Blumberg et al. | |
| 2013/0197127 A1 | 8/2013 | Wilken | |
| 2016/0303102 A1 | 10/2016 | Albayrak | |
| 2017/0114037 A1 | 4/2017 | Davis et al. | |
| 2017/0143721 A1 | 5/2017 | Wright et al. | |
| 2017/0231957 A1 | 8/2017 | Albayrak | |

FOREIGN PATENT DOCUMENTS

| | | |
|---|---|---|
| CN | 102579362 | 7/2012 |
| EP | 0 569 096 | 11/1993 |
| EP | 1 344 520 | 9/2003 |

(Continued)

OTHER PUBLICATIONS

International Preliminary Report on Patentability issued in corresponding International Application No. PCT/EP2015/063061, dated Dec. 21, 2017.

International Search Report and Written Opinion issued in corresponding International Application No. PCT/EP2015/063061, dated Feb. 22, 2016.

Balaraman et al., "Asenapine, a new sublingual atypical antipsychotic," *J. Pharmacol. Pharmacother.*, 1(1):60-61, 2010.

Beck et al., "A new long-acting injectable microcapsule system for the administration of progesterone," *Fertility and Sterility*, 31(5):545-551, 1979.

(Continued)

*Primary Examiner* — Michael B. Pallay
(74) *Attorney, Agent, or Firm* — Parker Highlander PLLC

(57) ABSTRACT

Provided is a process for the production of nano- and/or microparticles containing a therapeutically active agent embedded in a polymer matrix or encapsulated by a polymer shell, and nano- and/or microparticles obtainable by the process, said process comprising the steps of: a) providing a solution of a polymer selected from polylactide, polyglycolide, and polyester copolymers comprising copolymerized units of lactic acid and/or glycolic acid in an organic solvent SI having limited water solubility: b) providing a solution or dispersion of a therapeutically active agent in as solvent or mixture of organic solvents S2 comprising at least 50 vol. % benzyl alcohol, c) combining the solution or the solution and suspension provided in step a) and step b) to provide an organic phase which comprises dissolved polymer and dissolved therapeutically active agent in a mixture of the organic solvents S I and S2; d) agitating the organic phase provided in step c) in a vessel and adding an aqueous surfactant solution to the agitated organic phase in a volume ratio of at least 2:1 in terms of the total volume of the aqueous surfactant solution to the total volume of the organic phase as provided in step c), thus causing the formation of a dispersion containing a continuous aqueous phase and a discontinuous organic phase; and e) allowing the spontaneous formation of the nano- and/or microparticles via transfer of organic solvent from the discontinuous organic phase into the continuous aqueous phase directly after the dispersion has been formed.

19 Claims, 9 Drawing Sheets

(56) References Cited

FOREIGN PATENT DOCUMENTS

| JP | 2003 089631 | | 3/2003 | |
|---|---|---|---|---|
| WO | WO 1995/023600 | | 9/1995 | |
| WO | WO 1999/032108 | | 7/1999 | |
| WO | WO 2002/049619 | | 6/2002 | |
| WO | WO 2002/049620 | | 6/2002 | |
| WO | WO 2003/020245 | | 3/2003 | |
| WO | WO 2003/077887 | | 9/2003 | |
| WO | WO 2004/096259 | | 11/2004 | |
| WO | WO 2007/023495 | | 3/2007 | |
| WO | WO 2008/075320 | | 6/2008 | |
| WO | WO 2009/109844 | | 9/2009 | |
| WO | WO 2010/119455 | | 10/2010 | |
| WO | WO-2010119455 | A2 * | 10/2010 | ........... A61K 9/0024 |
| WO | WO 2010/149727 | | 12/2010 | |
| WO | WO 2011/159903 | | 12/2011 | |
| WO | WO 2012/066565 | | 5/2012 | |
| WO | WO 2012/070034 | | 5/2012 | |

OTHER PUBLICATIONS

Database WPI 2003-817239, Hanashima et al., "Sustained release external composition e.g. lotion or ointment, comprises medicine and base material having plasticity dispersed in nonporous polymer microparticle," and JP 2003 089631, Mar. 28, 2003.

Database WPI 2012-M75503, Shu et al., "Sustained-release microsphere comprises felodipine, ethyl cellulose, and drug release regulating agent, where the microsphere is prepared by emulsification method," and CN 102 579 362, Jul. 18, 2012.

Minassian et al., "Evaluation of the clinical efficacy of asenapine in schizophrenia," *Expert Opin Pharmacother.*, 11(12):2107-2115, 2010.

Nordstierna et al., "Molecular release from painted surfaces: free and encapsulated biocides," *Progress in Organic Coatings*, 69(1):45-48, 2010.

PCT International Search Report and Written Opinion issued in International Application No. PCT/EP2015/063049, dated Jul. 27, 2015.

PCT International Search Report and Written Opinion issued in International Application No. PCT/EP2014/076455, dated Jan. 29, 2015.

Sahana et al., "PLGA nanoparticles for oral delivery of hydrophobic drugs: influence of organic solvent on nanoparticle formation and release behavior in vitro and in vivo using estradiol as a model drug," *Journal of Pharmaceutical Sciences*, 97(4):1530-1542, 2008.

Stoner et al., "Asenapine: A Clinical Review of a Second-Generation Antipsychotic," *Clin. Therapeutics*, 34(5):1023-1040, 2012.

* cited by examiner

PROCESS FOR THE PREPARATION OF DRUG LOADED MICROPARTICLES

This application is a national phase application under 35 U.S.C. § 371 of International Application No. PCT/EP2015/063061, filed Jun. 11, 2015, the entire contents of which are hereby incorporated by reference.

This invention relates to a process for the production of nano- and/or microparticles containing a therapeutically active agent embedded in a polymer matrix or encapsulated by a polymer shell. The process is suitable for the provision of pharmaceutical formulations containing the nano- and/or microparticles, in particular long acting formulations. Advantageously, they can be administered as injectable long acting formulations.

Pharmaceutical formulations containing suitable drugs which are prepared by the process in accordance with the invention can be advantageously used to treat or prevent a variety of conditions, such as mental disorders, cancer, overactive bladder or postmenopausal disorders.

Especially mental disorders are typically chronic diseases and require the use of continuous medication. For example, schizophrenia is a lifelong psychotic disease. Non-adherence to antipsychotic medications of patients suffering from serious, persistent mental disorders remains a significant challenge. The success of the therapy depends very sensitively on patient compliance and adherence. One possibility to address this issue is the development of long acting injections. In addition to avoiding first pass effect and establishing a stable blood plasma concentration, they improve adherence to therapy and provide an effective means to ameliorate symptoms, prevent relapse and decrease hospitalization rates. Especially relapses can have serious consequences in a variety of clinical and functional domains.

The first long acting injections for antipsychotic drugs are based on formation of esters of active ingredients with a long chain fatty acid (such as decanoate or palmitate). Examples are haloperidol decanoate, fluphenazine decanoate, flupenthixol decanoate, pipothiazine palmitate and zuclopenthixol decanoate (prodrug). Due to the esterification with a fatty acid, the drug derivatives are soluble in oily vehicles (e.g., sesame or coconut oil). These solutions can be injected intramuscularly. The active ingredient can be made available via hydrolysis of the ester through endogenous plasma esterase. Such formulations are able to avoid first pass effect, to establish stable blood plasma concentration, to reduce undesired side effects. However, these formulations are also associated with significant side effects, including pain (Pharmacological Treatment in Schizophrenia, Future Medicine, Ed: Matcheri S Kesvan, 2012) and other injection-side reactions (Bloch et al., J. Clin. Psychiatry, 2001, 62, 855-859).

The second generation antipsychotic drugs with more favourable side effect profiles are developed. For the improvement of medication adherence, long acting injections are preferred (Antipsychotic long acting Injections, Ed: P. Haddad, T. Lambert and J. Lauriello, Oxford University Press, 2011).

Examples of currently available long acting injections of second generation antipsychotic drugs are:
1. Risperdal® Consta® (risperidone)

The long acting injection is based on microspheres containing biodegradable polymers, but a complex process is used to manufacture these microspheres. The controlled release of risperidone is planned for two weeks. The application of this formulation needs an additional application of an oral risperidone formulation.

2. Invega® (paliperidone palmitate, prodrug)

Paliperidone is released by hydrolysis of the paliperidone palmitate ester by endogenous plasma esterase. The formulation is based on a nanocrystalline suspension of the ester.

3. Zypadhera® (olanzapine pamoate salt)

Poorly soluble olanzapine pamoate in form of microcrystals suspended in an aqueous vehicle. When injected intramuscularly, the salt slowly dissolves and dissociates into separate molecules of olanzapine and pamoatic acid. This formulation is associated with critical side effects, like post-injection syndrome effects.

Known processes for the preparation of pharmaceutical formulations suitable for long acting injection formulations are complex, subject to limitations with respect to the drug to be formulated or the amount of drug contained in the formulation, and/or provide non-optimal results with respect to the administration of the formulation or the release of the active ingredient.

WO 02/49620 A2 discloses a process for the production of microparticles containing a non-water soluble biologically active as well as microparticles produced by this process. Microparticles containing a hydrophobic drug exhibited high encapsulation efficiency. The process can be carried out without a need for halogenated solvents, and allows the rapid formation of the desired microparticles while no complex equipment is needed. In addition, favourable release profiles of the active agent can be obtained. However, the drug load of the obtained particles was not always satisfactory for all therapeutic indications.

It was surprisingly found that the process in accordance with the present invention addresses such problems, and represents a versatile and effective tool for the preparation of drug loaded nano- and/or microparticles which can be suitably used in pharmaceutical formulations, in particular long acting injection formulations. The process of the invention allows the production of nano- and/or microparticles with a drug load that is sufficiently high to deliver an effective dose of the active agent over extended periods of time. Advantageous release profiles are obtained. At the same time, the process rapidly yields the desired particles.

To that extent, the present invention provides a process for the production of nano- and/or microparticles containing a therapeutically active agent embedded in a polymer matrix or encapsulated by a polymer shell, said process comprising the steps of:
  a) providing a solution of a polymer selected from polylactide, polyglycolide, and polyester copolymers comprising copolymerized units of lactic acid and/or glycolic acid in an organic solvent S1 having limited water solubility;
  b) providing a solution or a suspension of a therapeutically active agent in an organic solvent or mixture of organic solvents S2 comprising at least 50 vol. % benzyl alcohol;
  c) combining the solutions or the solution and the suspension provided in step a) and step b) to provide an organic phase which comprises dissolved polymer and dissolved or dispersed therapeutically active agent in a mixture of the organic solvents S1 and S2;
  d) agitating the organic phase provided in step c) in a vessel and adding an aqueous surfactant solution to the organic phase agitated in the vessel in a volume ratio of at least 2:1 in terms of the total volume of the aqueous surfactant solution to the total volume of the organic phase provided in step c), thus causing the formation of a dispersion containing a continuous aqueous phase and a discontinuous organic phase; and e) allowing the spontaneous formation of a suspension of the nano- and/or microparticles via transfer of organic solvent from the discontinuous organic phase into the continuous aqueous phase directly after the dispersion has been formed in step d).

The nano- and/or microparticles provided in step e) contain a therapeutically active agent embedded in a polymer matrix or encapsulated by a polymer shell, and said polymer matrix or polymer shell comprises the polymer selected from polylactide, polyglycolide, and polyester copolymers comprising copolymerized units of lactic acid and/or glycolic acid.

Surprisingly, it has been found that the use of benzyl alcohol, which has poor water solubility and is a solvent for the polymer used for microparticle manufacture, is advantageous for both high encapsulation efficiency and high drug content. The process in accordance with the invention is very versatile as regards the therapeutically active agent to be incorporated into the nano- and/or microparticles while high loads of the therapeutically active agent in the nano- and/or microparticles can be achieved. In addition the process can be conveniently carried out under mild conditions, and without the need for complex equipment. The process can be carried out as a simple one-pot process and it may readily be scaled up to meet commercial-scale production needs. Moreover, it is very efficient in that it enables a reduction of the energy and the time required for the production of the particles. In addition, comparably small amounts of solvents and surfactants as well as toxicologically acceptable solvents, in particular non-halogenated solvents, can be conveniently used.

Thus, contents of therapeutically active agent of more than 10 wt. %, preferably more than 15 wt. %, more preferably more than 20 wt. % and even more preferably more than 30 wt. % in the nano- and/or microparticles could be conveniently achieved by the process in accordance with the invention. Also the encapsulation efficiency, i.e. the ratio of the therapeutically active agent incorporated into the nano- and/or microparticles, is high, and typically 70% or more, preferably 75% or more, and more preferably 80% or more, in terms of the ratio (wt/wt) of the actual content of the active agent in the nano- and/or microparticles, divided by the theoretical content×100.

As will be understood by the skilled reader, the reference to "nano- and/or microparticles" indicates that the particles may be completely or predominantly in the nanometer size range (such as 10 to 100 nm), that they may be completely or predominantly in the micrometer size range (such as >0.1 to 1000 μm, or preferably >0.1 to 100 μm), or that particle mixtures of nano- and microparticles can be prepared in the context of the invention. The process according to the present invention provides convenient control of the particle size and the particle size distribution. Typically, the particle size of the nano- and/or microparticles in the context of the present invention as determined e.g. by laser scattering ranges from 10 nm to 1000 μm, preferably from 50 nm to 300 μm. The $d_{90}$ value, determined via laser scattering on a particle number basis, is preferably below 100 μm, more preferably below 50 μm. The mean particle diameter based on a particle volume basis generally ranges from 10 nm to 200 μm, preferably from 400 nm to 150 μm, more preferably from 1 μm to 125 μm, and in particular from 5 μm to 125 μm. The mean diameter is determined by laser scattering and calculated as volume weighted mean diameter that represents the arithmetic mean size in volume %, mode (D(4,3)).

The particle size, including the mean particle diameter, can be influenced by variety of process parameters. Thus, an increased amount of surfactant in the aqueous surfactant solution, or a more vigorous agitation, such as a faster stirring speed, favor smaller particle sizes. Furthermore, the particle size can be adjusted by using more diluted polymer solutions, or by using a viscosity modifier in the aqueous surfactant solution. Moreover, the particle size distribution, or the upper or the lower limit of the particle size, may be adjusted via conventional methods such as sieving or other forms of powder classification.

It is an advantage of the nano- and/or microparticles obtainable by the process in accordance with the invention that they are generally non-agglomerating. Preferably, the nano- and/or microparticles are nano- and/or microspheres.

The process in accordance with the invention is very versatile with respect to the nature of agent present in the nano- and/or microparticles.

It is preferred that the solubility of the therapeutically active agent benzyl alcohol is 10 g/L or higher, more preferably 30 g/L or higher, and even more preferably 100 g/L or higher at 20° C. In this context, the solubility is indicated as the weight of the dissolved substance (the solute) per volume of the solvent (i.e. the volume of solvent added to the solute) at a temperature of 20° C.

As will be understood by the skilled person, the indication for which a pharmaceutical formulation is used may have consequences for the type of formulation and for the drug content. In the context of the present invention, therapeutically active agents are preferably used which are suitable for the treatment or prevention of mental disorders, including dementia and neuropsychiatric disorders, cancer, postmenopausal disorders, or an overactive bladder. The advantages of the process of the invention are particularly pronounced for therapeutically active agents suitable to treat or prevent a mental disorder, i.e. preferably the therapeutically active agent is a psychoactive agent, and more preferably an antipsychotic agent.

Exemplary preferred active agents for use in the context of the present invention are selected from the group consisting of risperidone, paliperidone, aripiprazole, iloperidone, rivastigmine, duloxetine, donepezil, pramipexole, memantine, haloperidol, oxybutynine, naltrexone and raloxifene, including pharmaceutically acceptable salts of any of these therapeutic agents. Particularly preferred as therapeutically active agents are any one or more selected from risperidone, paliperidone, aripiprazole and pharmaceutically acceptable salts thereof.

On the other hand, asenapine and the salts thereof, in particular asenapine and pharmaceutically acceptable salts thereof, may be excluded as therapeutically active agents from use in the context of the present invention.

The nano- and/or micro-particles may contain a single therapeutic agent, or a combination of two or more therapeutically active agents. Thus, unless defined otherwise in, or dictated by a specific context, the generic reference to a therapeutically active agent herein encompasses the possibility that two or more therapeutically active agents are used.

As will be understood by the skilled person, pharmaceutically acceptable salt forms may be formed, e.g., by protonation of an atom carrying an electron lone pair which is susceptible to protonation, such as an amino group, with an inorganic or organic acid, or as a salt of a carboxylic acid group with a physiologically acceptable cation as they are well known in the art. Exemplary base addition salts comprise, for example, alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine, procaine salts, meglumine salts, diethanol amine salts or ethylenediamine salts; aralkyl amine salts such as N,N-dibenzylethylenediamine salts, benetamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctyl-ammonium salts or tetrabutylammonium salts; and basic amino acid salts such as arginine salts or lysine salts. Exemplary acid addition salts comprise, for example, mineral acid salts such as hydrochloride, hydrobromide, hydroiodide, sulfate salts, nitrate salts, phosphate salts (such as, e.g., phosphate, hydrogenphosphate, or dihydrogenphosphate salts), carbonate salts, hydrogencarbonate salts or perchlorate salts; organic acid salts such as acetate, propionate, butyrate, pentanoate, hexanoate, heptanoate, octanoate, cyclopentanepropionate, undecanoate, lactate, maleate, oxalate, fumarate, tartrate, malate, citrate, nicotinate, benzoate, salicylate, pamoate or ascorbate salts; sulfonate salts such as methanesulfonate, ethanesulfonate, 2-hydroxyethanesulfonate, benzenesulfonate, p-toluenesulfonate (tosylate), 2-naphthalenesulfonate, 3-phenylsulfonate, or camphorsulfonate salts; and acidic amino acid salts such as aspartate or glutamate salts.

The therapeutically active agent is usually contained in the nano- and/or micro-particles in an amount of 10 wt. % or more, preferably 15 wt. % or more, more preferably 20 wt. % or more, and most preferably 30 wt. % or more. The upper limit is not particularly limited, but in terms of practical considerations the amount is typically not more than 60 wt. %, and frequently not more than 50 wt. %. In this context, the content is indicated as the ratio of the weight of the active agent divided by the total weight of the nano- and/or microparticles. Moreover, it is indicated on the basis of the therapeutically active agent as such, i.e. its non-salt form, typically as the free base. Thus, e.g. in the case of a salt form of the active agent, or of a solvate, the determined amount is calculated as the corresponding amount of the active agent as such, typically the free base.

In the nano- and/or microparticles provided by the process in accordance with the invention, the therapeutically active agent is embedded in a polymer matrix or encapsulated by a polymer shell. The therapeutically active agent is embedded or encapsulated in a solid form, which may be a crystalline or amorphous form. Preferably, the therapeutically active agent is embedded in a polymer matrix in the form of a solid dispersion of the therapeutically active agent in the polymer matrix. This includes a crystalline dispersion (i.e. a form wherein the therapeutically active agent forms crystalline phases dispersed in the polymer matrix), an amorphous dispersion (i.e. a form wherein the therapeutically active agent forms amorphous phases in the polymer matrix), or a solid state solution (i.e. a form where the therapeutically active agent forms a molecular dispersion in the polymer matrix). In a solid dispersion of the therapeutically active agent in the polymer matrix, the therapeutically active agent may be dispersed across their full cross-section of the nano- and/or microparticles. However, for example if the nano- and/or microparticles carry a coating, there may be certain regions in the nano- and/or microparticles which remain free from the therapeutically active agent.

The therapeutically active agent may be present in the nano- and/or microparticles in molecular dispersed form, amorphous or crystalline form, including a solvate or a hydrate form.

The nano- and/or microparticles provided by the process in accordance with the invention contain a therapeutically active agent embedded in a polymer matrix or encapsulated by a polymer shell, and said polymer matrix or polymer shell comprises a polymer selected from polylactide, polyglycolide, and polyester copolymers comprising copolymerized units of lactic acid and/or glycolic acid. Such polymers are advantageously biodegradable, and thus suitable e.g. for parenteral injection. As will be understood, the reference to (co-)polymerized units of lactic acid and/or glycolic acid herein refers to the units as they are contained in the polymer, with bonds formed to adjacent units. However, (co)polymers of lactic acid and/or glycolic acid are typically obtained using lactide and/or glycolide as starting materials, and the (co) polymers are thus frequently referred to as "polyglycolide", "polylactide", "copolymer of lactide" with a given comonomer, or "copolymer of glycolide" with a given comonomer. In the context of the present application, (co)polymers obtained from other forms of polymerization starting from lactic acid and/or glycolic acid are not excluded by this terminology.

Such polymers are known to the skilled person and established for use in the medical field (e.g. Biodegradable polymers in clinical use and clinical Development, Edited by A. Domb, N. Kumar and A. Ezra, Wiley, 2011, Long Acting Injections and Implants Editors: J. C. Wright and D. J. Burgess, Springer 2012). Suitable polymers include polyglycolide homopolymers (PGA, also referred to as polyglycolic acid), and polylactide homopolymers (PLA, also referred to as polylactic acid). Since polymers formed from lactic acid as monomer units can contain the units in D- or L-configuration, lactic acid may form a homopolymer containing only one of the two enantiomers (e.g. poly(L-lactic acid), PLLA), or a polymer combining units of L- and D-lactic acid. The latter are also referred to as stereo-copolymers. The stereo-copolymers may have different arrangements of the comonomers, and form e.g. random or block copolymers (e.g. poly(DL-lactic acid) random copolymer, or L-lactic acid/DL-lactic acid copolymers. Such stereo-copolymers formed from lactic acid as monomer unit are also suitable for use in the context of the invention. Unless indicated otherwise in a specific context, reference to polymerized lactic acid or lactide units includes L-lactic acid units, D-lactic acid units, or combinations of the two. Moreover, unless indicated otherwise in a specific context, reference to polylactide homopolymers includes not only polymers consisting of D-lactic acid or L-lactic acid units, but also polymers combining D-lactic acid and L-lactic acid units.

As particularly suitable polyester copolymers comprising copolymerized units of lactic acid and/or glycolic acid, reference can be made to a copolymer of lactide and glycolide, i.e. poly(lactide-co-glycolide), also referred to as poly(lactic-co-glycolic acid), PLGA. As will be appreciated by the skilled person, the degradation rate of such polymers after administration can be controlled by the ratio of copolymerized units of lactic acid to glycolic acid in the copolymer. Among these poly(lactide-co-glycolide) copolymers, preferred are those wherein the content of polymerized lactic acid units is at least 50 mol %, and in particular those wherein the content of polymerized lactic acid units is 50 to 85 mol %, such as 50 or 75 mol %, based on the total amount of polymerized units. As examples of other suitable comonomers that may be present in polyester copolymers comprising copolymerized units of lactic acid and/or glycolic acid, one or more comonomers selected from tetramethylglycolide, δ-valerolactone, ε-caprolactone, trimethylene carbonate, tetramethylglycolide, and ethylene glycol may be mentioned. Thus, exemplary polyester copolymers, preferably binary copolymers, comprising copolymerized units of lactic acid and/or glycolic acid include a copolymer selected from the group consisting of a copolymer of glycolide and tetramethylglycolide, a copolymer of glycolide and δ-valerolactone, a copolymer of glycolide and ε-caprolactone, a copolymer of glycolide and trimethylene carbonate, a copolymer of lactide and tetramethylglycolide, a copolymer of lactide and δ-valerolactone, a copolymer of lactide and ε-caprolactone, a copolymer of lactide and trimethylene carbonate, a copolymer of glycolide and ethylene glycol, and a copolymer of lactide and ethylene glycol.

The polyester copolymers include random copolymers, block copolymers and gradient copolymers. Suitable block copolymer architectures include, e.g. AB block copolymers (e.g. AB block polymers comprising a polylactide (PLA) block and a poly(ethylene glycol) (PEG) block), ABA tri-block copolymers (e.g. ABA tri-block copolymers comprising PLA-PEG-PLA), star-shaped block copolymers (e.g. S(3)-PEG-PLA block copolymers and S(4)-PEG-PLA block copolymers).

In the polyester copolymers comprising copolymerized units of lactic acid and/or glycolic acid for use in the context of the present invention, it is preferred that the amount of the copolymerized units of lactic acid and/or glycolic acid (i.e. the amount of copolymerized units of lactic acid, if no glycolic acid is copolymerized, the amount of copolymerized units of glycolic acid, if no lactic acid is copolymerized, or the sum of the amounts of copolymerized units of glycolic acid and lactic acid, if both are copolymerized) accounts for at least 50 mol % of all copolymerized units in the copolymer. It is more preferred that that the amount of the copolymerized units of lactic acid and/or glycolic acid accounts for at least 70 mol % of all copolymerized units in the copolymer.

It will be appreciated by the skilled reader that the degradation rate of the nano- and/or microparticles of the invention can be influenced by the molecular weight of the polymer. Polymers of different molecular weights (or inherent viscosities) can be mixed to yield a desired degradation profile. Generally, polymers with an intrinsic viscosity in the range of 0.1 to 3 dL/g, preferably to 2 dL/g (0.1% (w/v), chloroform, at 25° C.) are used.

Particularly preferred for use in the context of the present invention are nano- and/or microparticles comprising a poly(lactide-co-glycolide) copolymer, i.e. a copolymer consisting of glycolic acid and lactic acid units. In terms of their relative amount of glycolic acid and lactic acid units, preferred are those wherein the content of polymerized lactic acid units is at least 50 mol %, and in particular those wherein the content of polymerized lactic acid units is 50 to 85 mol %, such as 50 or 75 mol %, based on the total amount of polymerized units. Blends of poly(lactide-co-glycolide) copolymers with different relative amounts of glycolic acid and lactic acid, favourably within the above preferred limits, may also be used.

Suitable commercially obtainable polymers for use in the nano- and/or microparticles according to the present invention include, but are not limited to Resomer® (EVONIK) L-104, L-206, L-207, L-208, L-209, L-210, L-214, R-104, R-202, R-203, R-206, R-207, R-208, G-110, G-205, LR-909, RG-502, RG-502H, RG-503, RG-503H, RG-504, RG 504H, RG-505, RG-505H, RG-506, RG-508, RG-752, RG-752H, RG-753, RG753H, RG-755, RG-756, RG-757 and Resomer® RG-858.

The polymer matrix or polymer shell of the nano- and/or microparticles may comprise one type of polymer selected from polylactide, polyglycolide, and polyester copolymers comprising copolymerized units of lactic acid and/or glycolic acid, or two or more types of polymers selected from polylactide, polyglycolide, and polyester copolymers comprising copolymerized units of lactic acid and/or glycolic acid, e.g. as a polymer blend. If two or more types are used, the polymers may differ e.g. in the type of polymerized monomer units, or in the relative ratios thereof. It is preferred that the one or more polymers selected from polylactide, polyglycolide, and polyester copolymers comprising copolymerized units of lactic acid and/or glycolic acid account for 70 wt. % or more, in particular 80 wt. % or more of the polymers in the polymer matrix or polymer shell of the nano- and/or microparticles. It is particularly preferred that the polymer matrix or polymer shell does not contain any other polymer component, apart from the one or more polymers selected from polylactide, polyglycolide, and polyester copolymers comprising copolymerized units of lactic acid and/or glycolic acid.

The nano- and/or microparticles prepared by the process in accordance with the invention comprise the therapeutically active agent embedded in a polymer matrix or encapsulated by a polymer shell. Optionally, they may comprise in addition excipients including, e.g., one or more selected from a colorant, a vehicle, a preservative, an antioxidant, a buffer, a surfactant and a flavoring agent. For example, optional additional components may be admixed within the particles, or coated onto the particles. It is preferred that the therapeutically active agent and the polymer selected from polylactide, polyglycolide, and polyester copolymers comprising copolymerized units of lactic acid and/or glycolic acid account for 80 wt. % or more, in particular 90 wt. % or more of the total weight of the nano- and/or microparticles. It is particularly preferred that the nano- and/or microparticles consist of (i) the therapeutically active agent and (ii) the polymer selected from polylactide, polyglycolide, and polyester copolymers comprising copolymerized units of lactic acid and/or glycolic acid, and (iii) optionally up to a maximum of 10 wt. %, preferably up to a maximum of 5 wt. %, based on the total weight of the nano- and/or microparticles, of one or more selected from surfactants, other excipients and residual solvent.

In step a) of the process in accordance with the invention, a solution is provided of a polymer selected from polylactide, polyglycolide, and polyester copolymers comprising copolymerized units of lactic acid and/or glycolic acid in an organic solvent S1 having limited water solubility.

The organic solvent S1 is a solvent for the polymer having limited water solubility. Preferably, the solubility of S1 in water is 1 to 60 wt. % (or 10 to 600 g/L) at 20° C. (as wt. % or weight of the solvent S in relation to the total weight of the mixed phase containing water and the solvent S1), more preferably 2 to 40 wt. % (20 to 400 g/L), and in particular 4 to 40 wt. % (40 to 400 g/L).

The solubilities of the polymers suitable for use in the context of the present invention in numerous organic solvents are reported in the literature or can be tested in a straightforward manner. The same applies for the miscibility or solubility of solvents in water, for which values can be derived from numerous standard collections of physical and chemical data, such as the CRC Handbook of Chemistry and Physics, Taylor & Francis. The following table provides an additional overview.

|  | boiling point* [° C.] | solubility in water** [g/L] (20° C.) |
| --- | --- | --- |
| ethyl formate | 54.5 | 105*** |
| ethyl acetate | 77.06 | 85.3 |
| methyl acetate | 57 | 319 |
| methyl formate | −31.5 | 300 |
| butyl acetate | 126.5 | 7 |
| n-propyl acetate | 101.6 | 21.2 |
| isopropyl acetate | 90 | 31 |
| n-propyl formate | 81.3 | 28 |
| glycofurol | 328 | soluble |
| methylisopropylketone | 94-95 | 6 |
| methyl ethyl ketone | 79.6 | 292 |
| dimethyl carbonate | 90-91 | 139 |

*Handbook of Chemistry and Physics, CRC Press, 65$^{th}$ edition, 1984-1985
**Merck Chemicals Product Information
***Gestis Stoffdatenbank Preferably, the polymer should be soluble in the solvent S1 in an amount of 100 g/L or more at 20° C. as the weight of the dissolved substance (the solute) per volume of the solvent (i.e. the volume of solvent added to the solute).

Preferred solvents S1 are selected from alkyl acetates, especially C1-C3 alkyl acetates, alkyl formates, especially C1-C3 alkyl formates, methyl ethyl ketone, and mixtures of two or more thereof. Particularly preferred are solvents S1 selected from ethyl acetate, methyl acetate, ethyl formate, propyl formate, isopropyl formate, methyl ethyl ketone and mixtures of two or more thereof. Generally, the solvent S1 and the solvent or mixture of organic solvents S2 are different solvents.

In step b) of the process in accordance with the invention, a solution or dispersion is provided of the therapeutically active agent in an organic solvent or mixture of organic solvents S2 comprising at least 50 vol. % benzyl alcohol. As will be understood, the term "organic solvent or mixture of organic solvents S2" may refer to benzyl alcohol alone, or to a mixture of benzyl alcohol with one or more other solvents, provided that the content of benzyl alcohol in S2 is at least 50 vol. %. The volume ratio is indicated on the basis of the total volume of S2, i.e. the sum of volumes of the benzyl alcohol with any additional solvent that may be used to provide S2, prior to their combination. While the influence of temperature on the ratio is low, the reference temperature for the volume ratio is generally 20° C. Preferably the organic solvent or mixture of organic solvents S2 contains at least 80 vol. % of benzyl alcohol, more preferably at least 90 vol. % benzyl alcohol, and most preferably S2 is benzyl alcohol. Any other solvent(s) that may be used in a mixture of organic solvents S2 should preferably be fully miscible with the benzyl alcohol. The suspension of the therapeutically active agent in S2 contains, in addition to the dissolved therapeutically active agent, the solid therapeutically active agent in dispersed form, i.e. remaining, non-dissolved amounts of the therapeutically active agent. For example, such a dispersion containing additional amounts of solid active agent may result if the therapeutically active agent is dissolved in the solvent or mixture of organic solvents S2 at a higher temperature to provide a saturated solution, and the saturated solution is subsequently used at a lower temperature. Another example is a solution prepared by dispersing amounts of the active agent in S2 which exceed the solubility thereof in S2. It is a characteristic of the process in accordance with the invention that any dispersed solid active agent is also efficiently incorporated into the nano- and/or microparticles.

It is an important characteristic of benzyl alcohol used in the process of the present invention that it can act as solvent for a wide range of organic molecules. Thus, benzyl alcohol generally acts as a solvent which helps to dissolve the therapeutically active agent fully or partially in the organic phase provided in step a). Preferably, the solubility of the therapeutically active agent in the organic solvent benzyl alcohol should be 10 g/L or higher, more preferably 30 g/L or higher, and even more preferably 100 g/L or higher at 200° C. In this context, the solubility is indicated as the weight of the dissolved substance (the solute) per volume of the solvent (i.e. the volume of solvent added to the solute). The following table provides an additional overview.

| Therapeutically active agent | Solubility [mg/mL] |
| --- | --- |
| Risperidone | 500 |
| Paliperidone | 233 (60° C.) |
| Aripiprazole | 400 |
| Iloperidone | 200 |
| Oxybutynin chloride | 1000 |
| Haloperidol | 110 |
| Rivastigmine tartrate | 200 |
| Duloxetine hydrochloride | 400 |
| Donepezil hydrochloride | 350 |
| Pramipexole dihydrochloride | 100 |
| Memantine hydrochloride | 130 |
| Naltrexone hydrochloride | 800 |

The organic solvent or mixture of organic solvents S2 should preferably be able to act also as a solvent for the polymer selected from polylactide, polyglycolide, and polyester copolymers comprising copolymerized units of lactic acid and/or glycolic acid. Preferably, the solubility of the polymer in the mixture of solvents S1+S2 in the proportions used in the process of the invention should be 100 g/L or higher at 20° C. as the weight of the dissolved substance (the solute) per volume of the solvent (i.e. the volume of solvent added to the solute).

The volume ratio of solvent or solvent mixture S2 to solvent S1 in the organic phase provided in step c) of the process of the invention, is preferably 5-50 vol. % S2 to 50-95 vol. % S1, based on the sum of the volumes S1+S2 prior to their combination as 100 vol. %. Particularly preferred are ratios of 20-50 vol. % S2 to 50-80 vol. % S1. It will be understood that the solvent S2 should preferably be miscible with the solvent S1 in the ratios in which these solvents are used. While the influence of temperature on the ratio is low, the reference temperature for the volume ratio is generally 20° C. Furthermore, the organic solvent or mixture of organic solvents S2 should preferably be miscible with the solvent S1 such that a single organic liquid phase is formed when the two solvents are combined to provide the organic phase in step c). Preferably, the ratio of solvent S2 to solvent S1 is suitably adjusted within the above ranges and preferred ranges, such that the solubility of the therapeutically active agent in the combined solvents S1+S2 is 10 g/L or higher at 20° C.

The organic phase provided in step c) of the process in accordance with the invention contains the mixture of organic solvents S1 and S2. Unless indicated otherwise, or dictated by a specific context, any reference to solvent S1 or solvent S2 is intended to include the option that more than one of S1 or S2, respectively, is used. Further solvents or water may be present in the organic phase in addition to S1 and S2, as far as they do not have a negative impact on the process. However, it is generally preferred that the solvent or solvent mixture used to provide the organic phase in step c) of the process in accordance with the invention contains at least 80, more preferably at least 90% (vol./vol., based on the total volume of solvents added to the vessel to provide the organic phase) of S2 and S1, and it is most preferred that the organic phase consists of S2 and S1. Moreover, it is generally preferred that no halogenated solvents are used in the process of the invention, e.g. as solvent in S1, in S2 or as any optional additional solvent.

As will be understood from the above, a preferred combination of solvents S1 and S2 is that solvent S1 is selected from ethyl acetate, methyl acetate, ethyl formate, propyl formate, isopropyl formate, methyl ethyl ketone and mixtures of two or more thereof, and S2 is benzyl alcohol.

The organic phase provided in step c) should contain a single organic liquid phase, i.e. does not form an emulsion or any other system containing two or more separate liquid phases. The polymer is dissolved in this liquid phase. The therapeutically active agent is dissolved in the organic liquid phase, or additional amounts of solid active agent may be dispersed in the organic phase, e.g. if particularly high amounts of the active agent are to be incorporated into the nano- and/or microparticles.

In the organic phase provided in step c) of the process in accordance with the invention, the content of the dissolved polymer is preferably 1 wt. % to 30 wt. %, based on the total weight of the organic phase. The concentration of the therapeutically active agent can be suitably chosen with a view to the content of the active agent in the resulting particles discussed above. Exemplary concentrations of the therapeutically active agent dissolved or dispersed in the organic phase range from 1 to 30 wt. %, based on the total weight of the organic phase including the active agent. As noted above, the process of the present invention is capable of incorporating the therapeutically active agent into the nano- and/or microparticles with a high efficiency, such that a high ratio of typically 70% or more, preferably 75% or more, and in particular 80% (wt/wt) or more of the therapeutically active agent dissolved or dispersed in the organic phase provided in step c) will be incorporated into the particles.

As will be understood, the ratio of the amount of therapeutically active agent dissolved or dispersed in the organic phase provided in step c) to the total amount of solids dissolved or dispersed in the organic phase (i.e. typically the total amount of the polymer dissolved in the organic phase and of therapeutically active agent dissolved or dispersed in the organic phase) is typically at least as high as the desired content of the therapeutically active agent in the nano- and/or microparticles. Thus, preferably the ratio of the amount of therapeutically active agent dissolved or dispersed in the organic phase provided in step c) to the total amount of solids dissolved or dispersed in the organic phase is usually 10 wt. % or more, preferably 15 wt. % or more, more preferably 20 wt. % or more, and most preferably 30 wt. % or more.

After the organic phase containing the polymer and the therapeutically active agent has been provided in step c), an aqueous surfactant solution is added thereto. The addition of the aqueous surfactant solution to the organic phase provided in step c) is carried out while the organic phase provided in step c) is agitated, preferably stirred. The aqueous surfactant solution may be added in a continuous manner, or in multiple steps. Preferably, the surfactant solution is added to the total volume of the organic phase such that the content of the surfactant solution in the combination of the surfactant solution and organic phase gradually increases until the addition is completed. The addition may take place e.g. over a time period of 5 s to 5 min, preferably 10 s to 2 min. Thus, a generally preferred form of the addition of the aqueous surfactant solution to the organic phase in step d) is to add the aqueous surfactant solution to the total volume of the organic phase under stirring such that the content of the surfactant solution in the combined surfactant solution and organic phase gradually increases until the addition is completed, and the addition takes place over a period of time of 5 s to 5 min, more preferably 10 s to 2 min. For example, the surfactant solution can be poured into the stirred organic phase over a time period of 5 s to 5 min, preferably 10 s to 2 min.

It is preferred for reasons of efficiency to provide the organic phase in step c) in a vessel with a volume that is sufficiently large to additionally accommodate the volume of the surfactant solution to be added. In this case, the process can be carried out as a one-pot process, i.e. a process where the organic phase containing the therapeutically active agent and the polymer is provided in a vessel in step c), and the aqueous surfactant solution is added to the same vessel in step d), such that the desired nano- and/or microparticles can be prepared in a single vessel in subsequent steps. Thus, steps c), d) and e) can take place in the same vessel.

The aqueous surfactant solution added in step d) contains water as the main solvent in the aqueous surfactant solution. Water can be the only solvent in the aqueous surfactant solution, but it is also possible to use a co-solvent. Preferably, the solvent(s) in the aqueous surfactant solution consist (s) of water or of water in combination with a co-solvent which is fully miscible in all proportions with water. Preferred examples are C1-C3 alcohols, such as ethanol. Moreover, it is preferred that none of the solvents S1 and S2 are contained in the aqueous surfactant solution prior to its addition to the organic phase provided in step c). The volume ratio of water in the aqueous surfactant solution is more than 50 vol. % of the total volume of solvents combined to form the aqueous surfactant solution, preferably more than 80 vol. %, and more preferably more than 90 vol. %. Reference temperature for the volume ratio is 20° C.

The concentration of the surfactant in the aqueous surfactant solution is preferably in the range of 0.1% (w/v) to 30% (w/v), preferably 0.1% to 20%, and more preferably 0.1 to 5%, based on the total volume of the surfactant solution. As will be understood by the skilled reader, the concentration in weight by volume corresponds to the amount of the solute in g per 100 ml of the total volume of the solution including the surfactant, typically at 20° C.

Surfactants suitable for the aqueous surfactant solution encompass cationic-, anionic-, and non-ionic surfactants. Exemplary surfactants can be selected from polyoxyethylene-polyoxypropylene block copolymers, in particular polyoxyethylene-polyoxypropylene-polyoxyethylene-triblock copolymers such as Poloxamer®, Poloxamine®, polyethylene glycol alkyl ethers, fatty acid esters of polyoxyethylenesorbitan, especially polyoxyethylenesorbitan monooleate and polyoxyethylenesorbitan monolaurate also referred to as polysorbates (Tween®, Span®), sucrose esters (Sistema®, Ryoto Sugar Ester, Tokyo), gelatin, polyvinylpyrrolidone, fatty alcohol polyglycosides, Charps, Charpso, decyl-β-D-glycopyranoside, decyl-β-D-maltopyranoside, dodecyl-β-D-maltopyranoside, sodium oleate, polyethylene glycol, polyvinyl alcohol (PVA), polyethoxylated fatty acid ethers (Brij®), Triton X 100 or mixtures thereof. Preferred as a surfactant are polyvinyl alcohol, polyoxyethylene-polyoxypropylene-polyoxyethylene-triblock copolymers and fatty acid esters of polyoxyethylenesorbitan, especially polyoxyethylenesorbitan monooleate and polyoxyethylenesorbitan monolaurate, or mixtures thereof.

The aqueous surfactant solution may contain other components besides the water, optional co-solvents and the surfactant, e.g. a buffer, or an agent for adjusting the viscosity of the aqueous surfactant solution, or an agent for adjusting the ion strength of the solution. For example, the aqueous surfactant solution may comprise a dissolved salt, such as NaCl, or dissolved sugar.

In the process according to the invention, the aqueous surfactant solution is added in step d) to the organic phase provided in step c) in a volume ratio of at least 2:1. The volume ratio is indicated in terms of the total volume of the aqueous surfactant solution to the total volume of the organic phase provided in step c) prior to the addition of the aqueous surfactant solution to the organic phase. Preferably, the volume ratio is at least 3:1. While it is possible to use very large volumes of the aqueous surfactant solution to prepare the nano- and/or microparticles, it is preferred to keep the volume at a low level in order to reduce the consumption of solvents and other components. Thus, the volume ratio of the total volume of the aqueous surfactant solution to the total volume of the organic phase is generally not more than 10:1, preferably not more than 5:1. The volume of the aqueous surfactant solution is typically sufficiently large that such that it can dissolve at least the solvent S1 contained in the organic phase to which the aqueous surfactant solution is added.

The addition of the aqueous surfactant solution to the organic phase at a volume ratio as defined above causes the formation of a dispersion containing a continuous aqueous phase and a discontinuous organic phase. Due to the water solubility at least of the solvent S1, the aqueous surfactant solution not only forms the continuous phase in the resulting dispersion, but acts at the same time as an extraction medium at least for the solvent S1 wherein the polymer had been dissolved. In addition, also a part of the benzyl alcohol, and optionally of further solvent(s) contained in S2 can be extracted to the aqueous phase. Thus, the solvent S1 and a least a part of the solvent or mixture of solvents S2 is transferred from the organic phase to the aqueous continuous phase.

This process may proceed via an emulsion of the organic phase as a discontinuous phase in the aqueous surfactant phase as an intermediate. However, since the solvent S1 is soluble in water to a certain extent, S1 is extracted from the organic phase into the continuous phase thereby leading to the formation of solid nano- and micro particles. Since this extraction occurs rapidly, a stable emulsion can typically not be observed in the process. Rather, once a continuous aqueous phase has been formed in step d) of the process in accordance with the invention, a suspension of the nano- and/or microparticles is directly formed in step e). A certain amount of solvents S1 and S2, including benzyl alcohol, may remain in the nano- and/or microparticles, and can be removed in (optional) subsequent extraction steps.

The transfer of organic solvent (generally solvent S1 and at least a part of the solvent or solvent mixture S2) occurs in step e) from the organic phase to the continuous aqueous phase, generally via diffusion of organic solvents into the aqueous phase, and via dissolution of the organic solvents in the aqueous phase. The polymer and the therapeutically active agent are left in the discontinuous organic phase, and a suspension of nano- and/or microparticles is formed in this manner. The formation of the suspension of nano- and/or microparticles typically takes place within minutes, or even less than a minute, after the start of the addition of the aqueous surfactant solution in step d). Typically, nano- and/or microparticles can be observed immediately after the formation of the dispersion containing a continuous aqueous phase and a discontinuous organic phase in step d). The formation of the suspension of nano- and/or microparticles takes place spontaneously directly after the dispersion containing a continuous aqueous phase and a discontinuous organic phase is formed in step d), i.e. without the need for any further activity triggering the formation, such as the removal of a solvent from the mixture e.g. via evaporation. However, further steps such as the extraction of solvents remaining in the nano- and/or microparticles, e.g. with a mixture of water and a co-solvent, or the removal of organic solvent(s) from the system during or after the formation of the suspension of nano- and/or microparticles, can be optionally added to the process in accordance with the invention. The organic solvent(s) can be removed, e.g., via evaporation or extraction methods known in the art.

It has been found that the size and the size distribution of the nano- and/or microparticles can be conveniently controlled in this process, e.g. by varying the energy of agitation during the addition of the aqueous phase, or by using viscosity modifiers, or by decreasing the polymer concentration or by varying the composition of the aqueous surfactant phase.

After the suspension of nano- and/or microparticles has been formed, the nano- and/or microparticles can be isolated from the liquid phase. They can be dried via conventional methods, including e.g. extraction, spray drying, fluid bed drying, freeze drying, centrifugation, evaporation and/or filtration. These methods can also be used to remove residues of S2 and/or S1, if necessary. Volatile solvents can be conveniently removed from the particles via evaporation. Less volatile solvents can be removed by other methods established in the art, such as extraction. Washing steps can also be added to the process of the invention as needed. A particularly convenient step in order to obtain a dry, reconstitutable powder containing the nano- and/or microparticles is lyophilisation.

The nano- and/or microparticles containing the therapeutically active agent can be conveniently stored e.g. as dry powders.

The nano- and/or microparticles prepared by the process in accordance with the invention can be used as a medicament and specifically as a medicament for treatment of the human or animal body by therapy. In particular if the therapeutically active agent is a preferred therapeutic agent selected from psychoactive therapeutic agents, including antipsychotic agents, they can be used in the treatment or prevention of a mental disorder, and specifically dementia, depression, bipolar disorder or a psychotic disorder, such as schizophrenia. Preferred antipsychotic therapeutic agents for the treatment or prevention of schizophrenia and bipolar disorder are risperidone, paliperidone, aripiprazol, haloperidol or iloperidone (including any therapeutically acceptable salt form of these). A preferred active agent for the treatment or prevention of depression is duloxetine (including any therapeutically acceptable salt form thereof). Preferred active agents for the treatment or prevention of dementia, including Alzheimer's disease or Parkinson's disease are donepezil, memantine, rivastigmine, or pramipexole (including any therapeutically acceptable salt form of these). Other preferred indications, depending on the active agent, are the treatment or prevention of a postmenopausal disorder, or of an overactive bladder. A preferred active agent for the treatment or prevention of postmenopausal diseases is raloxifene (including any therapeutically acceptable salt form thereof). A preferred active agent for the treatment or prevention of an overactive bladder is oxybutynine (including any therapeutically acceptable salt form of these). A preferred active agent for the treatment of addiction is naltrexone (including any therapeutically acceptable salt form thereof).

Preferably, the medicament is a depot medicament, in particular a long acting injection medicament. Such a depot medicament or long acting injection medicament is a medicament which contains an amount of the therapeutically active agent that is sufficient to provide a therapeutic plasma level of the active agent over an extended period of time, such as 1 week or more, preferably 2 weeks or more in the body of the subject to which the depot medicament or long acting injection medicament is administered. To that extent, the nano- and/or microparticles for use as a medicament are preferably to be administered in intervals of at least 1 week, preferably at least 2 weeks, and more preferably at least 4 weeks between consecutive administrations. Typically, the treatment involving the administration in these intervals extends over periods of several months or years, i.e. more than one month, or more than one year. The nano- and/or microparticles can be advantageously administered via the parenteral route, preferably via parenteral injection, and in particular via subcutaneous or intramuscular injection.

Thus, the nano- and/or microparticles prepared in accordance with the invention can also be comprised in a pharmaceutical formulation, and a further aspect of the invention concerns a process for the preparation of a pharmaceutical formulation comprising a first step of preparing nano- and/or microparticles with the process of the present invention as disclosed above, and a subsequent step of forming a pharmaceutical formulation comprising these nano- and/or microparticles. The step of forming the pharmaceutical formulation can comprise, e.g., the combination of the nano- and/or microparticles prepared in the first step with one or more pharmaceutically acceptable excipients, and/or the provision of units containing a predetermined dose of the therapeutically active agent, and/or the packaging of units containing a predetermined dose of the therapeutically active agent.

Preferably, the pharmaceutical formulation is a depot formulation. Such a depot formulation is a formulation which contains an amount of the therapeutically active agent that is sufficient to provide a therapeutic plasma level of the active principle over an extended period of time, such as 1 week or more, preferably 2 weeks or more in the body of the subject to which the depot formulation is administered, i.e. preferably the formulation is to be administered in intervals of at least 1 week, preferably at least 2 weeks and more preferably at least 4 weeks, between consecutive administrations. To that extent, the invention also provides a process for the preparation of a pharmaceutical formulation as defined above, which formulation is to be administered in intervals of at least 1 week, preferably at least 2 weeks, between consecutive administrations. Typically, the treatment involving the administration in these intervals extends over periods of several months or years, i.e. more than one month, or more than one year. The formulation can be advantageously administered via the parenteral route, preferably via parenteral injection, and in particular via subcutaneous or intramuscular injection. If, in accordance with the preferred embodiments discussed above, the therapeutically active agent is a psychoactive therapeutic agent to treat or prevent a mental disorder, and in particular an antipsychotic therapeutic agent, the formulation can be used in the treatment or prevention of a mental disorder or a neuropsychiatric disorder, in particular in the treatment or prevention of schizophrenia or bipolar disorder.

In addition to the nano- and/or microparticles, the pharmaceutical formulation prepared in accordance with the present invention may contain one or more pharmaceutically acceptable excipients. Exemplary pharmaceutically acceptable excipients that may be used in the formulation of the pharmaceutical compositions are selected from carriers, vehicles, diluents, in particular water, e.g. in the form of water for injection, or in the form of a physiological salt solution, other solvents such as monohydric alcohols, such as ethanol, or isopropanol, and polyhydric alcohols such as glycols and edible oils such as soybean oil, coconut oil, olive oil, safflower oil cottonseed oil, oily esters such as ethyl oleate, isopropyl myristate; binders, adjuvants, solubilizers, thickening agents, stabilizers, disintegrants, lubricating agents, buffering agents, emulsifiers, wetting agents, suspending agents, sweetening agents, colourants, flavours, preservatives, antioxidants, processing agents, drug delivery modifiers and enhancers such as calcium phosphate, magnesium stearate, talc, monosaccharides, disaccharides, starch, gelatine, cellulose, methylcellulose, sodium carboxymethyl cellulose, dextrose, hydroxypropyl-$\beta$-cyclodextrin, polyvinylpyrrolidone or polyethylene glycol. Other suitable pharmaceutically acceptable excipients are described in Remington's Pharmaceutical Sciences, 15th Ed., Mack Publishing Co., New Jersey (1991). It will be understood that the excipient(s) need to be selected in accordance with the planned route of administration. A preferred formulation in accordance with the present invention is a liquid formulation suitable for parenteral injection, comprising the nano- and/or microparticles in accordance with the invention in dispersed form. Suitable liquid phases for liquid formulations for parenteral administration are well known in the art. The liquid phase typically comprises water, in particular in the form of water for injection or in the form of a physiological salt solution, and optionally further adjuvants selected e.g. from a buffer, an acid or a base for adjusting the pH, a dispersing agent, a surfactant, an agent for adjusting the viscosity, and combinations thereof. Exemplary components of such a liquid formulation are water for injection Tween 20 or Tween 80 as surfactants, sodium carboxymethyl cellulose, mannitol, dextran, acids or bases like acetic acid, citric acid, or NaOH, or salts like NaCl.

The pharmaceutical formulation, in particular the formulation for parenteral injection in accordance with the invention preferably contains the nano- and/or microparticles in an amount of 2 to 60 wt. %, based on the total weight of the formulation, more preferably of 5 to 50 wt. %.

As regards the administration of the nano- and/or microparticles prepared in accordance with the invention or the pharmaceutical composition prepared in accordance with the invention, it had been noted above that the administration occurs advantageously via the parenteral route. Preferred is the intramuscular or subcutaneous administration, and particular preferred is intramuscular injection. For example, the injection may be made in the gluteal or deltoid muscles.

The dose of the nano- and or microparticles, or the pharmaceutical preparation to be administered will be determined by the attending physician and clinical factors. As is well known in the medical arts, dosages for any one patient depends upon many factors, including factor such as the patient's size, body weight, age, sex, general health, individual response of the patient to be treated, and the severity of the disorder to be treated. For example, the dose may be selected such that the administered amount of the active agent, calculated as the free base, ranges from 50 to 1000 mg.

As will be understood, the mention of a treatment or prevention herein generally refers to the treatment or prevention of a disorder in an animal, preferably a mammal, and in particular a human subject. Similarly, any reference to the administration of the nano- or microparticles of the invention, or of a medicament or a pharmaceutical formulation comprising them generally refers to the administration to an animal (including a human and non-human animal), preferably a mammal, and most preferably to a human subject.

Moreover, the term "treatment" of a disorder or disease as used herein is well known in the art. "Treatment" of a disorder or disease implies that a disorder or disease is suspected or has been diagnosed in a patient/subject. A patient/subject suspected of suffering from a disorder or disease typically shows specific clinical and/or pathological symptoms which a skilled person can easily attribute to a specific pathological condition (i.e., diagnose a disorder or disease).

The "treatment" of a disorder or disease may, for example, lead to a halt in the progression of the disorder or disease (e.g., no deterioration of symptoms) or a delay in the progression of the disorder or disease (in case the halt in progression is of a transient nature only). The "treatment" of a disorder or disease may also lead to a partial response (e.g., amelioration of symptoms) or complete response (e.g., disappearance of symptoms) of the subject/patient suffering from the disorder or disease. Accordingly, the "treatment" of a disorder or disease may also refer to an amelioration of the disorder or disease, which may, e.g., lead to a halt in the progression of the disorder or disease or a delay in the progression of the disorder or disease. Such a partial or complete response may be followed by a relapse. It is to be understood that a subject/patient may experience a broad range of responses to a treatment (such as the exemplary responses as described herein above). The treatment of a disorder or disease may, inter alia, comprise curative treatment (preferably leading to a complete response and eventually to healing of the disorder or disease.

The term "prevention" of a disorder or disease as used herein is also well known in the art. For example, a patient/subject suspected of being prone to suffer from a disorder or disease may particularly benefit from a prevention of the disorder or disease. The subject/patient may have a susceptibility or predisposition for a disorder or disease, including but not limited to hereditary predisposition. Such a predisposition can be determined by standard methods or assays, using, e.g., genetic markers or phenotypic indicators. It is to be understood that a disorder or disease to be prevented in accordance with the present invention has not been diagnosed or cannot be diagnosed in the patient/subject (for example, the patient/subject does not show any clinical or pathological symptoms). Thus, the term "prevention" comprises the use of compounds of the present invention before any clinical and/or pathological symptoms are diagnosed or determined or can be diagnosed or determined by the attending physician.

Important aspects of the invention disclosed above shall in addition be summarized below:

1. A process for the production of nano- and/or microparticles containing a therapeutically active agent embedded in a polymer matrix or encapsulated by a polymer shell, said process comprising the steps of:

a) providing a solution of a polymer selected from polylactide, polyglycolide, and polyester copolymers comprising copolymerized units of lactic acid and/or glycolic acid in an organic solvent S1 having limited water solubility;

b) providing a solution or dispersion of a therapeutically active agent in an organic solvent or mixture of organic solvents S2 comprising at least 50 vol. % benzyl alcohol, c) combining the solutions or the solution and the suspension provided in step a) and step b) to provide an organic phase which comprises dissolved polymer and dissolved or dispersed therapeutically active agent in a mixture of the organic solvents S1 and S2;

d) agitating the organic phase provided in step c) in a vessel and adding an aqueous surfactant solution to the organic phase agitated in the vessel in a volume ratio of at least 2:1 in terms of the total volume of the aqueous surfactant solution to the total volume of the organic phase as provided in step c), thus causing the formation of a dispersion containing a continuous aqueous phase and a discontinuous organic phase; and e) allowing the formation, typically spontaneous formation, of a suspension of the nano- and/or microparticles via transfer of organic solvent from the discontinuous organic phase into the continuous aqueous phase directly after the dispersion has been formed in step d).

2. The process of item 1, wherein the therapeutically active agent is a therapeutically active agent suitable to treat or prevent a mental disorder, cancer, an overactive bladder, or a postmenopausal disorder.

3. The process of any of item 1, wherein the therapeutically active agent is an antipsychotic therapeutic agent.

4. The process of item 1, wherein the therapeutically active agent is selected from the group consisting of risperidone, paliperidone, aripiprazole, iloperidone, rivastigmine, duloxetine, donepezil, memantine, pramipexole, haloperidol, raloxifene, naltrexone and oxybutynine or from pharmaceutically acceptable salts of any of these therapeutic agents.

5. The process of item 4, wherein the therapeutically active agent is selected from the group consisting of risperidone, paliperidone, and aripiprazole, or from pharmaceutically acceptable salts of any of these therapeutic agents.

6. The process of item 1, wherein the therapeutically active agent has a solubility in benzyl alcohol at 20° C. of 10 g/L or higher.

7. The process of any of items 1 to 6, wherein the therapeutically active agent is contained in the nano- and/or microparticles in an amount of 10 wt. % or more, based on the total weight of the nano- and/or microparticles.

8. The process of item 7, wherein the therapeutically active agent is contained in the nano- and/or microparticles in an amount of 15 wt. % or more, based on the total weight of the nano- and/or microparticles.

9. The process of item 7, wherein the therapeutically active agent is contained in the nano- and/or microparticles in an amount of 20 wt. % or more, based on the total weight of the nano- and/or microparticles.

10. The process of item 7, wherein the therapeutically active agent is contained in the nano- and/or microparticles in an amount of 30 wt. % or more, based on the total weight of the nano- and/or microparticles.

11. The process of any of items 1 to 10, wherein the therapeutically active agent is dispersed as an amorphous or crystalline solid in a polymer matrix.

12. The process of any of items 1 to 11, wherein the polymer matrix or polymer shell of the prepared particles comprises a polymer selected from the group consisting of a polyglycolide homopolymer, a polylactide homopolymer, a copolymer of glycolide and lactide, a copolymer of glycolide and tetramethylglycolide, a copolymer of glycolide and δ-valerolactone, a copolymer of glycolide and ε-caprolactone, a copolymer of glycolide and trimethylene carbonate, a copolymer of lactide and tetramethylglycolide, a copolymer of lactide and δ-valerolactone, a copolymer of lactide and ε-caprolactone, a copolymer of lactide and trimethylene carbonate, a copolymer of glycolide and ethylene glycol, and a copolymer of lactide and ethylene glycol.

13. The process of item 12, wherein the polymer matrix or polymer shell of the prepared particles comprises a poly(lactide-co-glycolide) copolymer.

14. The process of any of items 1 to 13, wherein the solvent or mixture of solvents S2 comprises at least 80 vol. % of benzyl alcohol.

15. The process of any of items 1 to 13, wherein the solvent S2 is benzyl alcohol.

16. The process of any of items 1 to 15, wherein the solubility of the solvent S1 in water is 10 to 600 g/L.

17. The process of any of items 1 to 15, wherein the solubility of the solvent S1 in water is 20 to 400 g/L.

18. The process of any of items 1 to 17, wherein the solvent S1 is selected from alkyl acetates, alkyl formates, methyl ethyl ketone, and mixtures of two or more thereof.

19. The process of item 18, wherein the solvent S1 is selected from ethyl acetate, methyl acetate, ethyl formate, propyl formate, isopropyl formate, methyl ethyl ketone and mixtures of two or more thereof.

20. The process of any of items 1 to 19, wherein the ratio of solvent or mixture of organic solvents S2 to solvent S1 in the organic phase provided in step c) of the process of the invention is 5-50 vol. % S2 to 50-95 vol. % S1, based on the sum of the volumes S1+S2 prior to their combination as 100 vol. %.

21. The process of any of items 1 to 20, wherein the volume ratio of the total volume of the aqueous surfactant solution added in step d) to the total volume of the organic phase, prior to the addition, ranges from 2:1 to 5:1, preferably from 3:1 to 5:1.

22. The process of items 1 to 21, wherein the volume of the aqueous surfactant solution added in step d) is sufficiently large that at least the solvent S1 can be dissolved in the aqueous surfactant solution.

23. The process of any of items 1 to 22, wherein the aqueous surfactant solution is added in step d) by adding the aqueous surfactant solution to the total volume of the organic phase under stirring such that the content of the surfactant solution in the combined surfactant solution and organic phase gradually increases until the addition is completed.

24. The process of any of items 1 to 23, wherein the addition of the aqueous surfactant phase takes place over a time period of 5 s to 5 min, preferably 10 s to 2 min.

25. The process of any of items 1 to 24, wherein steps c), d) and e) take place in the same vessel.

26. The process of any of items 1 to 25, wherein the transfer of organic solvent from the discontinuous organic phase into the continuous aqueous phase in step e) takes place via diffusion of organic solvent into the aqueous surfactant phase and dissolution of organic solvent in the aqueous surfactant phase.

27. The process of any of items 1 to 28, wherein the surfactant in the aqueous surfactant solution added in step d) is selected from polyvinyl alcohol, polyoxyethylene-polyoxypropylene-polyoxyethylene-triblock copolymers and fatty acid esters of polyoxyethylenesorbitan, or mixtures thereof.

28. The process of any of items 1 to 27, wherein the prepared nano- and or microparticles have a mean particle diameter determined by laser scattering, within the size range of 1 μm to 125 μm on the basis of particle volume.

29. The process of any of items 1 to 28, further comprising a step of isolating the nano- and/or microparticles contained in the suspension formed in step e) from the liquid phase.

30. The process of any of items 1 to 29, further comprising a step of drying the nano- and/or microparticles.

31. The process of any of items 1 to 30, wherein:
the solvent S1 is selected from ethyl acetate, methyl acetate, ethyl formate, propyl formate, isopropyl formate, methyl ethyl ketone and mixtures of two or more thereof;
the solvent S2 is benzyl alcohol;
and the therapeutically active agent is selected from the group consisting of risperidone, paliperidone, aripiprazole, iloperidone, rivastigmine, duloxetine, donepezil, memantine, pramipexole, haloperidol, raloxifene, naltrexone and oxybutynine or from a pharmaceutically acceptable salt of any of these therapeutic agents.

32. The process of item 31, wherein the aqueous surfactant phase is added in step d) by pouring the aqueous surfactant phase into the organic phase while the organic phase is stirred, and the addition of the aqueous surfactant phase takes place over a time period of 5 s to 2 min, preferably 10 s to 2 min.

33. A process for the preparation of a pharmaceutical formulation comprising a first step of preparing nano- and/or microparticles in accordance with the process of any of items 1 to 32, and a subsequent step of forming a pharmaceutical formulation comprising the prepared nano- and/or microparticles.

34. The process of item 33, wherein the step of forming a pharmaceutical formulation comprising the prepared nano- and/or microparticles comprises one or more of i) to iii):
i) the combination of the nano- and/or microparticles prepared in the first step with one or more pharmaceutically acceptable excipients,
ii) the provision of units containing a predetermined dose of the therapeutically active agent, and/or
iii) the packaging of units containing a predetermined dose of the therapeutically active agent.

35. The process of item 33 or 34, wherein the pharmaceutical formulation is for use in the treatment or prevention of a mental disorder, including a neuropsychiatric disorder, a postmenopausal disorder, or an overactive bladder.

36. The process of any of items 33 to 35, wherein the pharmaceutical formulation is a depot formulation or a long acting injection formulation.

37. The process of item 36, wherein formulation is to be administered in intervals of at least 1 week between consecutive administrations.

38. The process of any of items 33 to 37, wherein the formulation is to be administered via the parenteral route.

39. The process of item 38 wherein the formulation is to be administered via subcutaneous or intramuscular injection.

40. Nano- and/or microparticles which are obtainable by the process of any of items 1 to 32.

41. A pharmaceutical formulation obtainable by the process for the preparation of a pharmaceutical formulation of any of items 33 to 39.

42. Nano- and/or microparticles which are obtained by the process of any of items 1 to 32.

43. A pharmaceutical formulation obtained by the process for the preparation of a pharmaceutical formulation of any of items 33 to 39.

EXAMPLES

Content of Therapeutically Active Agent (Active Principle) in Nano- and/or Microparticles In order to determine the content of the therapeutically active agent (active principle) in the nano- and/or microparticles (Core Loading), freeze dried nano- and/or microparticles were dissolved in acetonitrile. A portion of the solution was filtered through a 0.2 μm syringe filter for quantification of the therapeutically active agent by means of RP-HPLC.

The following determination of the theoretical active principle content and about the mean diameter were used for all examples.

Theoretical Active Principle Content in Nano- and/or Microparticles

The theoretical active principle content ("theoretical content") reflects the maximum active principle content. It is calculated from the masses of all educts present in the final formulation. Thus the theoretical content is defined as mass of the drug base divided by the sum of (mass API formulation+mass polymer+mass excipients)·100%.

The mass of excipients includes surfactants, as well as the residual organic solvent(s) used for the solubilization of the API as well as the polymers. The total mass of excipients present in the nano- and/or microparticles is approximated to about 5% of the sum of the masses of API formulation and polymer. Thus the mass excipient is defined as 0.05·(m API formulation+m polymer)

Encapsulation Efficiency

The Encapsulation Efficiency is defined as quotient of the active principle content and theoretical active principle content·100%

Mean Diameter

The size distribution of nano- and microparticles is determined by laser scattering and from these data the mean diameter is calculated as volume weighted mean diameter that represents the arithmetic mean size in volume % mode (D(4,3)).

Example 1

2.1 g of polymer Resomer® RG755S and 0.90 g of Polymer Resomer® RG503H were dissolved in 9 mL ethyl formate and transferred to a double-walled glass vessel (inside height 16.0 cm, inside diameter 4.6 cm). 2000 mg paliperidone were dissolved in 8.6 mL benzyl alcohol at 60° C. After cooling down to room temperature the API solution was added to the polymer solution. The paliperidone solution was dispersed in the polymer solution by means of a mechanical agitator (Dispermat FT, VMA-Getzmann GmbH, Germany, equipped with a 3 cm dissolver disc) for 14 min at 3000 rpm and for 22 min at 4000 rpm and for 50 s min at 3500 rpm at room temperature.

100 mL PVA solution (1.0% (w/v)) in 50 mM phosphate buffer pH 7.4 containing 5% (v/v) ethanol was added as continuous phase during agitation at 3000 rpm. After about 60 seconds of agitation, the suspension of nano- and microparticles was transferred to a 3 L beaker and 1 L PVA solution (2% (w/v) in 20 mM phosphate buffer pH 7.4 was added. The suspension was stirred magnetically. After 15 min 100 mL ethanol was added. After 60 min nano- and microparticles were collected by filtration. Nano and microparticles were transferred to a 3 L beaker and were diluted by addition of 1 L PVA solution (2% (w/v)) in 20 mM phosphate buffer pH 7.4. After 30 min 300 mL of a mixture consisting of 150 mL ethanol and 150 mL PVA solution (2% (w/v) in 20 mM phosphate buffer pH 7.4 was added. After 30 min a mixture of 135 mL ethanol and 65 mL PVA solution (2% (w/v) in 20 mM phosphate buffer pH 7.4 was added. This was repeated twice.

Subsequently, 100 mL ethanol was added after 30 min and after 60 min.

After 4 hours nano- and microparticles were collected by filtration. Subsequently, nano- and microparticles were diluted by addition of 1 L poloxamer 188 solution (4% (w/v)) in 20 mMmM phosphate pH 7.4 and by addition of 50 mL ethanol. The addition of ethanol was repeated three times. After 60 min the nano- and microparticles were separated and washed by filtration and concentrated to the desired volume. The suspension was stored frozen until lyophilisation.

The lyophilisate, resuspended in water contained nano- and micro particles with active principle content of 31.5% and with an encapsulations efficiency of 80.1%. The nano- and microparticles had a mean diameter of 33.4 μm.

The in-vitro release profile of the formulation was measured.

In vitro dissolution was performed with the aid of Sotax AT7 apparatus (Sotax AG, Switzerland). The dissolution apparatus is compliant with the USP 2 method (Paddle), described in the guidelines of the United States Pharmacopoeia. Dissolution studies were performed in 1-litre round-bottom glass vessels at a temperature of 37° C. with stainless steel paddle blades rotating at 50 rpm. Dissolution studies were carried out in 700 mL HEPES-buffered saline (11.9 g/L 4-(2-hydroxyethyl)-1-piperazineethanesulfonic acid, 2.9 g/L sodium chloride, 0.1% (v/v) Polysorbate 80, 0.01 g/L sodium azide) at pH 7.0. 15 mg of drug-loaded microparticles were placed into the glass vessels prior the addition of the initial dissolution medium. At 0, 4, 20 hours and 3, 4, 6 and 7 days, a 2 mL aliquot was removed for analysis. Samples were withdrawn using an injection needle with a syringe filter (regenerated cellulose) connected to a 2 mL-syringe. The sample volume was replenished with the same volume of fresh medium to keep the initial dissolution volume constant. The fresh medium was back-injected through the syringe filter so retained particles were washed back into the dissolution vessel. The amount of paliperidone released during the sampling period was determined by means of HPLC.

FIG. 1 shows the in-vitro release profile of Example 1

Example 2

1.8 g of polymer Purasorb and 1.2 g of polymer Purasorb 5004A were dissolved in 9 ml ethyl formate. The polymer solution was transferred to a double-walled glass vessel (inside height 16.0 cm, inside diameter 4.6 cm). 2000 mg paliperidone were dissolved in 8.6 mL benzyl alcohol at 60° C. After cooling down to room temperature the API solution was added to the polymer solution. The paliperidon solution was dispersed in the polymer solution by means of a mechanical agitator (Dispermat FT, VMA-Getzmann GmbH, Germany, equipped with a 3 cm dissolver disc) for 14 min at 3000 rpm and for 20.5 min at 4000 rpm and for 30 s at 3500 rpm at room temperature.

100 mL PVA solution (1.0% (w/v)) in 50 mM phosphate buffer pH 7.4 containing 5% (v/v) ethanol was added as continuous phase during agitation at 3500 rpm.

After about 60 seconds of agitation, the suspension of nano- and microparticles was transferred to a 3 L beaker and 1000 mL PVA solution (2% (w/v)) in 20 mM phosphate buffer pH 7.4 was added. The suspension was stirred magnetically. After 15 min 100 mL ethanol was added. Nano- and microparticles were collected after 70 min by filtration. The filter cake was transferred to a 3 L beaker and was diluted by addition of 1 L PVA solution (2% (w/v)) in 20 mM phosphate buffer pH 7.4. The extraction of organic solvents ethyl formate and benzyl alcohol was continued as described for example 1.

The suspension was stored frozen until lyophilisation.

The lyophilisate, resuspended in water contained nano- and microparticles with active principle content of 31.9% and with an encapsulations efficiency of 81.2%. The nano- and microparticles had a mean diameter of 47.8 µm.

The in-vitro release profile of the formulation was measured as described for example 1 (FIG. 2).

Example 3

3.0 g of polymer Resomer® RG504H was dissolved in 10 ml methyl acetate. The polymer solution was transferred to a double-walled glass vessel (inside height 16.0 cm, inside diameter 4.6 cm). 1400 mg paliperidone was dissolved in 6.0 mL benzyl alcohol at 60° C. After cooling down to room temperature the API solution was added to the polymer solution.

The paliperidone solution was dispersed in the polymer solution by means of a mechanical agitator (Dispermat FT, VMA-Getzmann GmbH, Germany, equipped with a 3 cm dissolver disc) for 5 min at 2000 rpm and for 7.5 min at 3000 rpm at room temperature.

80 mL PVA solution (1.0% (w/v)) in 50 mM phosphate buffer pH 7.4 containing 5% (w/v) NaCl was added as continuous phase during agitation at 3000 rpm.

After about 60 seconds of agitation, the suspension of nano- and microparticles was transferred to a 3 L beaker and 500 mL PVA solution (2% (w/v)) in 20 mM phosphate buffer pH 7.4 was added. The suspension was stirred magnetically. Another 500 mL PVA solution was added after 30 min. The suspension was stirred magnetically. After 20 min nano- and microparticles were collected by filtration. Subsequently, nano- and microparticles were diluted by addition of 1 L PVA solution (2% (w/v)) containing 5% NaCl (w/v) in 20 mM phosphate buffer pH 7.4. Another 300 mL of that PVA solution was added after 60 min. A mixture of 100 mL ethanol and 100 mL poloxamer 188 solution was added after 30 min, after 60 min, and after 90 min. 100 mL ethanol was added after 30 min and after 60 min.

After 4 hours nano- and microparticles were collected by filtration. Subsequently, nano- and microparticles were diluted by addition of 1 L poloxamer 188 solution (4% (w/v)) in 20 mM phosphate pH 7.4 and by addition of 50 mL ethanol. The addition of ethanol was repeated three-times. After 1 hour the nano- and microparticles were separated by filtration and concentrated to the desired volume. The suspension was stored frozen until lyophilisation.

The lyophilisate, resuspended in water contained nano- and micro particles with active principle content of 24.8% and with an encapsulations efficiency of 75.6%. The nano- and microparticles had a mean diameter of 33.6 µm.

The in-vitro release profile of the formulation was measured as described for example 1 (FIG. 3).

Example 4

2.55 g of polymer Resomer® RG755S and 0.45 g of Polymer Resomer® RG503H were dissolved in 9 ml methyl acetate. The polymer solution was transferred to a double-walled glass vessel (inside height 16.0 cm, inside diameter 4.6 cm). 2000 mg paliperidone were dissolved in 8.6 mL benzyl alcohol at 60° C. After cooling down to room temperature the API solution was added to the polymer solution. The paliperidone solution was dispersed in the polymer solution by means of a mechanical agitator (Dispermat FT, VMA-Getzmann GmbH, Germany, equipped with a 3 cm dissolver disc) for 14 min at 3000 rpm and for 15 min at 4000 rpm at room temperature.

100 mL PVA solution (1.0% (w/v)) containing 5% NaCl (w/v) in 50 mM phosphate buffer pH 7.4 was added as continuous phase during agitation at 4000 rpm.

After about 60 seconds of agitation, the suspension of nano- and microparticles was transferred to a 3 L beaker and 1000 mL PVA solution (2% (w/v)) in 20 mM phosphate buffer pH 7.4 was added. Extraction of organic solvents ethyl formate and benzyl alcohol was performed as described for Example 1.

The lyophilisate, resuspended in water contained nano- and microparticles with active principle content of 31.4% and with an encapsulations efficiency of 80.1%. The nano- and microparticles had a mean diameter of 43.9 µm.

The in-vitro release profile of the formulation was measured as described for example 1 (FIG. 4).

Example 5

2.55 g of polymer Resomer® RG755S and 0.45 g of Polymer Resomer® RG503H were dissolved in a solvent mixture comprising 6 mL ethyl formate and 6 mL ethyl acetate, and the solution was transferred to a double-walled glass vessel (inside height 16.0 cm, inside diameter 4.6 cm). 2000 mg paliperidone were dissolved in 8.6 mL benzyl alcohol at 60° C. After cooling down to room temperature the API solution was added to the polymer solution. The paliperidone solution was dispersed in the polymer solution by means of a mechanical agitator (Dispermat FT, VMA-Getzmann GmbH, Germany, equipped with a 3 cm dissolver disc) for 14 min at 3000 rpm and for 28.75 min at 4000 rpm at room temperature.

100 mL PVA solution (1.0% (w/v)) in 50 mM phosphate buffer pH 7.4 containing 5% (v/v) ethanol was added as continuous phase during agitation at 4000 rpm. After about 45 seconds of agitation, the suspension of nano- and microparticles was transferred to a 3 L beaker and 1 L PVA solution (2% (w/v)) in 20 mM phosphate buffer pH 7.4 was added. The suspension was stirred magnetically. After 15 min 100 mL ethanol was added. After 70 min nano- and microparticles were collected by filtration. Nano and microparticles were transferred to a 3 L beaker and were diluted by addition of 1 L PVA solution (2% (w/v) in 20 mM phosphate buffer pH 7.4). After 30 min 300 mL of a mixture consisting of 150 mL ethanol and 150 mL PVA solution (2% (w/v) in 20 mM phosphate buffer pH 7.4) was added. After 30 min a mixture of 135 mL ethanol and 65 mL PVA solution (2% (w/v) in 20 mM phosphate buffer pH 7.4) was added. This was repeated twice.

Subsequently, 100 mL ethanol was added after 30 min and after 60 min.

After 4 hours nano- and microparticles were collected by filtration. Subsequently, nano- and microparticles were diluted by addition of 1 L poloxamer 188 solution (4% (w/v)) in 20 mMmM phosphate pH 7.4 and by addition of 50 mL ethanol. The addition of ethanol was repeated three times. After 60 min the nano- and microparticles were separated and washed by filtration and concentrated to the desired volume. The suspension was stored frozen until lyophilisation.

The lyophilisate, resuspended in water contained nano- and micro particles with active principle content of 33.9% and with an encapsulations efficiency of 86.9%. The nano- and microparticles had a mean diameter of 35.8 µm.

The in-vitro release profile of the formulation was measured as described in example 1 (FIG. 5).

Example 6

2.55 g of polymer Resomer® RG755S and 0.45 g of Polymer Resomer® RG503H were dissolved in 9 mL ethyl formate, and the solution was transferred to a double-walled glass vessel (inside height 16.0 cm, inside diameter 4.6 cm). 2000 mg paliperidone were dissolved in 8.6 mL benzyl alcohol at 60° C. After cooling down to room temperature the API solution was added to the polymer solution. The paliperidone solution was dispersed in the polymer solution by means of a mechanical agitator (Dispermat FT, VMA-Getzmann GmbH, Germany, equipped with a 3 cm dissolver disc) for 14 min at 3000 rpm and for 11 min at 4000 rpm and for 40 s at 3500 rpm at room temperature.

100 mL PVA solution (1.0% (w/v)) in 50 mM phosphate buffer pH 7.4 containing 5% (v/v) ethanol was added as continuous phase during agitation at 3500 rpm. After about 45 seconds of agitation, the suspension of nano- and microparticles was transferred to a 3 L beaker and 1 L PVA solution (2% (w/v)) in 20 mM phosphate buffer pH 7.4 was added. The suspension was stirred magnetically. Subsequently the extraction and separation process was conducted as described in example 5.

The lyophilisate, resuspended in water contained nano- and micro particles with active principle content of 34.1% and with an encapsulations efficiency of 81.5%. The nano- and microparticles had a mean diameter of 46.6 Mm.

The in-vitro release profile of the formulation was measured as described for example 1 (FIG. 6).

Example 7

2.55 g of polymer Resomer® RG755S and 0.45 g of Polymer Resomer® RG503H were dissolved in 9 mL methyl acetate and the solution was transferred to a double-walled glass vessel (inside height 16.0 cm, inside diameter 4.6 cm). 2000 mg paliperidone were dissolved in 8.6 mL benzyl alcohol at 60° C. After cooling down to room temperature the API solution was added to the polymer solution. The paliperidone solution was dispersed in the polymer solution by means of a mechanical agitator (Dispermat FT, VMA-Getzmann GmbH, Germany, equipped with a 3 cm dissolver disc) for 14 min at 3000 rpm and for 14.5 min at 4000 rpm and for 10 s at 3000 rpm at room temperature.

100 mL PVA solution (1.0% (w/v)) in 50 mM phosphate buffer pH 7.4 containing 5% (w/v) NaCl was added as continuous phase during agitation at 3000 rpm. After about 45 seconds of agitation, the suspension of nano- and microparticles was transferred to a 3 L beaker and 1 L PVA solution (2% (w/v)) in 20 mM phosphate buffer pH 7.4 was added. The suspension was stirred magnetically. Subsequently the extraction and separation process was conducted as described in example 5.

The lyophilisate, resuspended in water contained nano- and micro particles with active principle content of 36.9% and with an encapsulations efficiency of 94.2%. The nano- and microparticles had a mean diameter of 61.1 µm.

The in-vitro release profile of the formulation was measured as described for example 1 (FIG. 7).

Example 8

1.5 g of polymer Resomer® RG755S and 1.5 g of polymer Resomer® RG753S were dissolved in a mixture of 9.5 ml ethyl formate and 0.5 mL ethanol. The polymer solution was transferred to a double-walled glass vessel (inside height 16.0 cm, inside diameter 4.6 cm). The API solution containing 1400 mg paliperidone in 6.0 ml benzyl alcohol was dispersed in the polymer solution by means of a mechanical agitator (Dispermat FT, VMA-Getzmann GmbH, Germany, equipped with a 3.0 cm dissolver disc) for 5 min at 2000 rpm and for 12 min at 3000 rpm at room temperature.

100 mL PVA solution (1.0% (w/v)) in 50 mM phosphate buffer pH 7.4 containing 5% (w/v) ethanol was added as continuous phase during agitation at 3000 rpm.

After about 60 seconds of agitation, the suspension of nano- and microparticles was transferred to a 3 L beaker and 1 L PVA solution (2% (w/v)) in 20 mM phosphate buffer pH 7.4 was added. The suspension was stirred magnetically. After 15 min 100 mL ethanol was added and after 40 min nano- and microparticles were collected by filtration. Subsequently, nano- and microparticles were diluted by addition of 1 L PVA solution (2% (w/v)) in 20 mM phosphate buffer pH 7.4. The suspension was stirred magnetically. The organic solvents ethyl formate and benzyl alcohol were removed by extraction.

After 40 min a mixture comprising 150 mL ethanol and 150 mL PVA solution solution (2% (w/v)) in 20 mM phosphate buffer pH 7.4 was added. After 25 min a mixture comprising 67 mL ethanol and 123 mL PVA solution solution (2% (w/v)) in 20 mM phosphate buffer pH 7.4 was added This step was repeated twice. Extraction was continued by addition of 100 mL ethanol after 25 min and after 50 min. After 25 min nano- and microparticles were collected by filtration. Subsequently, nano- and microparticles were diluted by addition of 1000 mL poloxamer 188 solution (4% (w/v)) in 20 mM phosphate pH 7.4 and 50 mL ethanol. Another volume of 50 mL ethanol was added after 15 min, 30 min and 45 min. After 60 min nano- and micro particles were separated by filtration and concentrated to the desired volume. The suspension was stored frozen until lyophilisation.

The lyophilisate, resuspended in water contained nano- and micro particles with active principle content of 24.9% and with an encapsulations efficiency of 76.6%. The nano- and microparticles had a mean diameter of 34.4 µm.

Example 9

1.5 g of polymer Resomer® RG753S and 1.5 g of Polymer Resomer® RG752S were dissolved in 10 ml ethyl formate. 1500 mg paliperidone were dissolved in 8.9 mL benzyl alcohol at 48° C. After cooling down to room temperature the API solution was added to the polymer solution. The homogeneous solution of the polymers and paliperidone was stirred magnetically for 17.17 hours. The obtained suspension of paliperidone crystals was transferred to a double-walled glass vessel (inside height 16.0 cm, inside diameter 4.6 cm) and the suspension was dispersed by means of a mechanical agitator (Dispermat FT, VMA-Getzmann GmbH, Germany, equipped with a 3 cm dissolver disc) for 10 min at 2000 rpm and for 5 min at 2500 rpm and for 15 min at 3000 rpm and for 6 min at 4000 rpm and for 5 min at 5000 rpm and finally for 1 min at 2500 rpm at room temperature.

100 mL PVA solution (1.0% (w/v)) in 50 mM phosphate buffer pH 7.4 was added as continuous phase during agitation at 2500 rpm.

After about 60 seconds of agitation, the suspension of nano- and microparticles was transferred to a 3 L beaker and 1000 mL PVA solution (2% (w/v)) in 20 mM phosphate buffer pH 7.4 was added. Extraction of organic solvents ethyl formate and benzyl alcohol was performed as described for Example 2.

The lyophilisate, resuspended in water contained nano- and microparticles with active principle content of 25.3% and with an encapsulations efficiency of 77.3%. The nano- and microparticles had a mean diameter of 41.1 μm.

Example 10

3.0 g of polymer Resomer® RG755S was dissolved in 10 mL ethyl formate and transferred to a double-walled glass vessel (inside height 16.0 cm, inside diameter 4.6 cm). The API solution containing 1.5 g risperidone in 6 mL benzyl alcohol was dispersed in the polymer solution by means of a mechanical agitator (Dispermat FT, VMA-Getzmann GmbH, Germany, equipped with a 3.0 cm dissolver disc) for 6 min at 3000 rpm at room temperature. 70 mL PVA solution (2.0% (w/v)) in water was added as continuous phase during agitation at 3000 rpm.

After about 60 seconds of agitation, the suspension of nano- and microparticles was transferred to a 3 L beaker and 400 mL PVA solution (2% (w/v)) in water was added. The suspension was stirred magnetically. The organic solvents ethyl formate and benzyl alcohol were removed by extraction. Additional volumes of PVA solution (2% (w/v)) were added after 30 min (200 mL), after 60 min (400 mL), and after 90 min (100 mL). Subsequently 140 mL ethanol was added after 30 min. This step was repeated three-times.

After 4 hours nano- and microparticles were collected by filtration. Washing was performed by addition of 1 L PVA solution (0.1% (w/v)) in 50 mM phosphate pH 5.5.

Nano- and microparticles were stored frozen until lyophilisation.

The lyophilisate, resuspended in water contained nano- and microparticles with active principle content of 26.9% and with an encapsulations efficiency of 75.9%. The nano- and microparticles had a mean diameter of 52.6 μm.

The in-vitro release profile of the formulation was measured. In vitro dissolution was performed using a Sample and Separate-Method in a hot cabinet at 37° C. in combination with a multi-position magnetic stirring plate. Dissolution studies were carried out in 100 mL amber wide neck glass bottles with screw lid in combination with a dissolution medium of 100 mL phosphate buffered saline (8 g/L sodium chloride, 0.2 g/L potassium chloride, 1.44 g/L disodium hydrogen phosphate dehydrate, 0.2 g/L potassium dihydrogen phosphate, 0.05 g/L sodium azide) at pH 7.4 continuously stirred at 300 rpm. 17 mg of drug-loaded microparticles were introduced into the glass bottles prior the addition of the initial dissolution medium. Dissolution samples of 2 mL were collected at 0, 4, 24 hours and every next day for a total release time period of 128 hours. Prior to the collection, the stirring was paused for half an hour to enable the microparticles to settle down. The sample volume was replenished with the same volume of fresh medium to keep the initial dissolution volume constant.

The amount of released drug was measured by HPLC.

FIG. 8 shows the in-vitro release profile of Example 10.

Example 11

3.0 g of polymer Resomer® RG755S was dissolved in 16.5 mL ethyl formate and transferred to a double-walled glass vessel (inside height 16.0 cm, inside diameter 4.6 cm). The API solution containing 1.5 g risperidone in 8 mL benzyl alcohol was dispersed in the polymer solution by means of a mechanical agitator (Dispermat FT, VMA-Getzmann GmbH, Germany, equipped with a 3.0 cm dissolver disc) for 17.5 min at 3000 rpm at room temperature.

150 mL PVA solution (1.0% (w/v)) in water containing 2.5% ethanol was added as continuous phase during agitation at 3000 rpm.

After about 60 seconds of agitation, the suspension of nano- and microparticles was transferred to a 3 L beaker and 850 mL PVA solution (1% (w/v)) in 50 mM phosphate buffer pH 7.0 was added. The suspension was stirred magnetically. The organic solvents ethyl formate and benzyl alcohol were removed by extraction. After 60 min 50 mL ethanol was added and after 30 min an additional volume of 1 L PVA solution (1% (w/v)) in 50 mM phosphate buffer pH 7.0 was added. After 2 hours the nano- and microparticles were collected by filtration. Washing was performed by addition of 2 L PVA solution (0.1% (w/v)) in 50 mM phosphate pH 5.8.

Nano- and microparticles were stored frozen until lyophilisation.

The lyophilisate, resuspended in water contained nano- or micro particles with active principle content of 31.8% and with an encapsulations efficiency of 80.9%. The nano- and microparticles had a mean diameter of 54.6 μm.

The in-vitro release profile was measured as described for Example 10 (FIG. 9).

Example 12

3.2 g of polymer Resomer® RG755S was dissolved in 10 ml ethyl formate and transferred to a double-walled glass vessel (inside height 16.0 cm, inside diameter 4.6 cm).

The API solution containing 1.5 g aripiprazole in 9.0 mL benzyl alcohol was dispersed in the polymer solution by means of a mechanical agitator (Dispermat FT, VMA-Getzmann GmbH, Germany, equipped with a 3.0 cm dissolver disc) for 22 min at 3000 rpm at room temperature. 70 mL PVA solution (1.0-% (w/v)) containing 5% (w/v) ethanol was added as continuous phase during agitation at 3000 rpm.

After about 60 seconds of agitation, the suspension of nano- and microparticles was transferred to a 3 L beaker and 1 L PVA solution (2% (w/v)) was added. The organic solvents ethyl formate and benzyl alcohol were removed by extraction as described for example 24.

The lyophilisate, resuspended in water contained nano- and microparticles with active principle content of 31.8% and with an encapsulations efficiency of 93.9%. The nano- and microparticles had a mean diameter of 46.7 μm.

The in-vitro release profile of the formulation was measured.

In vitro dissolution was performed using a Sample and Separate-Method in a hot cabinet at 37° C. in combination with a multi-position magnetic stirring plate. Dissolution studies were carried out in 1000 mL amber glass bottles with 600 mL Tris-buffered saline (3 g/L tris(hydroxymethyl) aminomethane, 5.8 g/L sodium chloride, 0.05% Polysorbate 80, 0.01% (w/v) sodium azide) at pH 7.4 continuously stirred at 150 rpm. 7 mg of drug-loaded microparticles were introduced into the glass bottles prior the addition of the dissolution medium. Dissolution samples of 2 mL were collected at 0, 4, 8, 24, 48 h and at two and three day intervals. Prior to the collection, the stirring was paused for half an hour to enable the microparticles to settle down. The sample volume was replenished with the same volume of fresh medium to keep the initial dissolution volume constant.

The amount of released drug was measured by HPLC.

Example 13

3.2 g of polymer Resomer® RG755S was dissolved in 10 ml ethyl formate and transferred to a double-walled glass vessel (inside height 16.0 cm, inside diameter 4.6 cm).

The API solution containing 1.5 g aripiprazole in 9.0 mL benzyl alcohol was dispersed in the polymer solution by means of a mechanical agitator (Dispermat FT, VMA-Getzmann GmbH, Germany, equipped with a 3.0 cm dissolver disc) for 45 min at 3000 rpm at room temperature. 70 mL PVA solution (1.0% (w/v)) containing 5% (w/v) ethanol was added as continuous phase during agitation at 3000 rpm.

After about 60 seconds of agitation, the suspension of nano- and microparticles was transferred to a 3 L beaker and 1 L PVA solution (2% (w/v)) was added. The organic solvents ethyl formate and benzyl alcohol were removed by extraction as described for example 20.

The lyophilisate, resuspended in water contained nano- or microparticles with active principle content of 31.2% and with an encapsulations efficiency of 92.9%. The nano- and microparticles had a mean diameter of 58.0 µm.

Example 14

1.6 g of polymer Resomer® RG755S and 1.6 g of polymer Resomer® RG753S were dissolved in 10 mL methyl acetate and transferred to a double-walled glass vessel (inside height 16.0 cm, inside diameter 4.6 cm).

The API solution containing 1.5 g aripiprazole in 9.0 mL benzyl alcohol was dispersed in the polymer solution by means of a mechanical agitator (Dispermat FT, VMA-Getzmann GmbH, Germany, equipped with a 3.0 cm dissolver disc) for 10 min at 3000 rpm and for 19 min at 4000 rpm at room temperature.

70 mL PVA solution (1.0-% (w/v)) containing 5% (w/v) ethanol was added as continuous phase during agitation at 3000 rpm.

After about 60 seconds of agitation, the suspension of nano- and microparticles was transferred to a 3 L beaker and 1 L PVA solution (2% (w/v)) was added. The organic solvents methyl acetate and benzyl alcohol were removed by extraction as described for example 20.

The lyophilisate, resuspended in water contained nano- and microparticles with active principle content of 31.1% and with an encapsulations efficiency of 93.8%. The nano- and microparticles had a mean diameter of 64.4 µm.

Example 15

1.6 g of polymer Resomer® RG755S and 1.6 g of polymer Resomer® RG752S were dissolved in 10 mL methyl acetate and transferred to a double-walled glass vessel (inside height 16.0 cm, inside diameter 4.6 cm).

The API solution containing 1.5 g aripiprazole in 9.0 mL benzyl alcohol was dispersed in the polymer solution by means of a mechanical agitator (Dispermat FT, VMA-Getzmann GmbH, Germany, equipped with a 3.0 cm dissolver disc) for 11 min at 3000 rpm and for 24 min at 4000 rpm at room temperature.

70 mL PVA solution (1.0-% (w/v)) containing 5% (w/v) ethanol was added as continuous phase during agitation at 1500 rpm.

After about 60 seconds of agitation, the suspension of nano- and microparticles was transferred to a 3 L beaker and 1 L PVA solution (2% (w/v)) was added. The suspension was stirred magnetically. Nano- and microparticles were separated by filtration after 10 min. The nano- and microparticles were transferred to a 3 L beaker and diluted by addition of 1 L PVA solution (2% (w/v)). The organic solvents methyl acetate and benzyl alcohol were removed by extraction as described for example 20.

The lyophilisate, resuspended in water contained nano- and microparticles with active principle content of 30.4% and with an encapsulations efficiency of 92.1%. The nano- and microparticles had a mean diameter of 98.4 µm.

Example 16

3.2 g of polymer Resomer® RG755S was dissolved in 10 ml methyl acetate and transferred to a double-walled glass vessel (inside height 16.0 cm, inside diameter 4.6 cm). The API solution containing 2.0 g aripiprazole in 12.0 mL benzyl alcohol was dispersed in the polymer solution by means of a mechanical agitator (Dispermat FT, VMA-Getzmann GmbH, Germany, equipped with a 3.0 cm dissolver disc) for 15 min at 3000 rpm and for 25 min at 4000 rpm at room temperature.

70 mL PVA solution (1.0-% (w/v)) containing 5% (w/v) ethanol was added as continuous phase during agitation at 3000 rpm.

After about 60 seconds of agitation, the suspension of nano- and microparticles was transferred to a 3 L beaker and 1 L PVA solution (2% (w/v)) was added. The suspension was stirred magnetically. After 60 min 300 mL of that PVA solution was added.

After 30 min a mixture of 200 mL PVA solution (2% (w/v)) and 200 mL ethanol was transferred to the beaker. This was repeated twice. Subsequently, 100 mL ethanol was added after 30 min and another 100 mL after 90 min. The organic solvents ethyl acetate and benzyl alcohol were removed by extraction.

After 5 hours nano- and microparticles were collected by filtration. Subsequently, nano- and microparticles were diluted by addition of 1 L poloxamer 188 solution (4% (w/v)) and 50 mL ethanol. Ethanol addition was repeated three-times. After 60 min the nano- and microparticles were separated by filtration and concentrated to the desired volume. The suspension was stored frozen until lyophilisation.

The lyophilisate, resuspended in water contained nano- and microparticles with active principle content of 37.7% and with an encapsulations efficiency of 93.4%. The nano- and micro-particles had a mean diameter of 50.3 µm.

Example 17

3.0 g of polymer Resomer® RG756S were dissolved in 12 mL ethyl acetate and transferred to a double-walled glass vessel (inside height 16.0 cm, inside diameter 3.4 cm). The API solution containing 350 mg iloperidone in 2.0 mL benzyl alcohol was dispersed in the polymer solution by means of a mechanical agitator (Dispermat FT, VMA-Getzmann GmbH, Germany, equipped with a 2.5 cm dissolver disc) for 20 min at 3000 rpm at room temperature. 100 mL PVA solution (1.0-% (w/v)) in 50 mM phosphate buffer pH 8.0 was added as continuous phase during agitation at 3000 rpm.

After about 60 seconds of agitation, the suspension of nano- and microparticles was transferred to a 3 L beaker and 1 L PVA solution (1% (w/v)) in 50 mM phosphate buffer pH 8.0 was added. The suspension was stirred magnetically and the organic solvents ethyl acetate and benzyl alcohol were removed by extraction. After 15 min and after 30 min 100 mL ethanol was added.

After 60 min the nano- and microparticles were collected by filtration. Nano- and microparticles were washed with 500 mL water and concentrated to the desired volume. The suspension was stored frozen until lyophilisation.

The lyophilisate, resuspended in water contained nano- and microparticles with active principle content of 10.3% and with an encapsulations efficiency of 90.1%. The nano- and micro-particles had a mean diameter of 42.6 m.

Example 18

3.0 g of polymer Resomer® RG756S were dissolved in 12 mL ethyl acetate and transferred to a double-walled glass vessel (inside height 16.0 cm, inside diameter 3.4 cm). The API solution containing 800 mg iloperidone in 4.0 mL benzyl alcohol was dispersed in the polymer solution by means of a mechanical agitator (Dispermat FT, VMA-Getzmann GmbH, Germany, equipped with a 2.5 cm dissolver disc) for 26 min at 3000 rpm at room temperature. 100 mL PVA solution (1.0% (w/v)) in 50 mM phosphate buffer pH 8.0 was added as continuous phase during agitation at 3000 rpm.

After about 60 seconds of agitation, the suspension of nano- and microparticles was transferred to a 3 L beaker and 1 L PVA solution (1% (w/v)) in 50 mM phosphate buffer pH 8.0 was added. The suspension was stirred magnetically and the organic solvents ethyl acetate and benzyl alcohol were removed by extraction. After 15 min and after 30 min 100 mL ethanol was added.

After 60 min the nano- and microparticles were collected by filtration. Nano- and microparticles were washed with 500 mL water and concentrated to the desired volume. The suspension was stored frozen until lyophilisation.

The lyophilisate, resuspended in water contained nano- and microparticles with active principle content of 20.4% and with an encapsulations efficiency of 92.5%. The nano- and micro-particles had a mean diameter of 44.8 m

Figure 1:
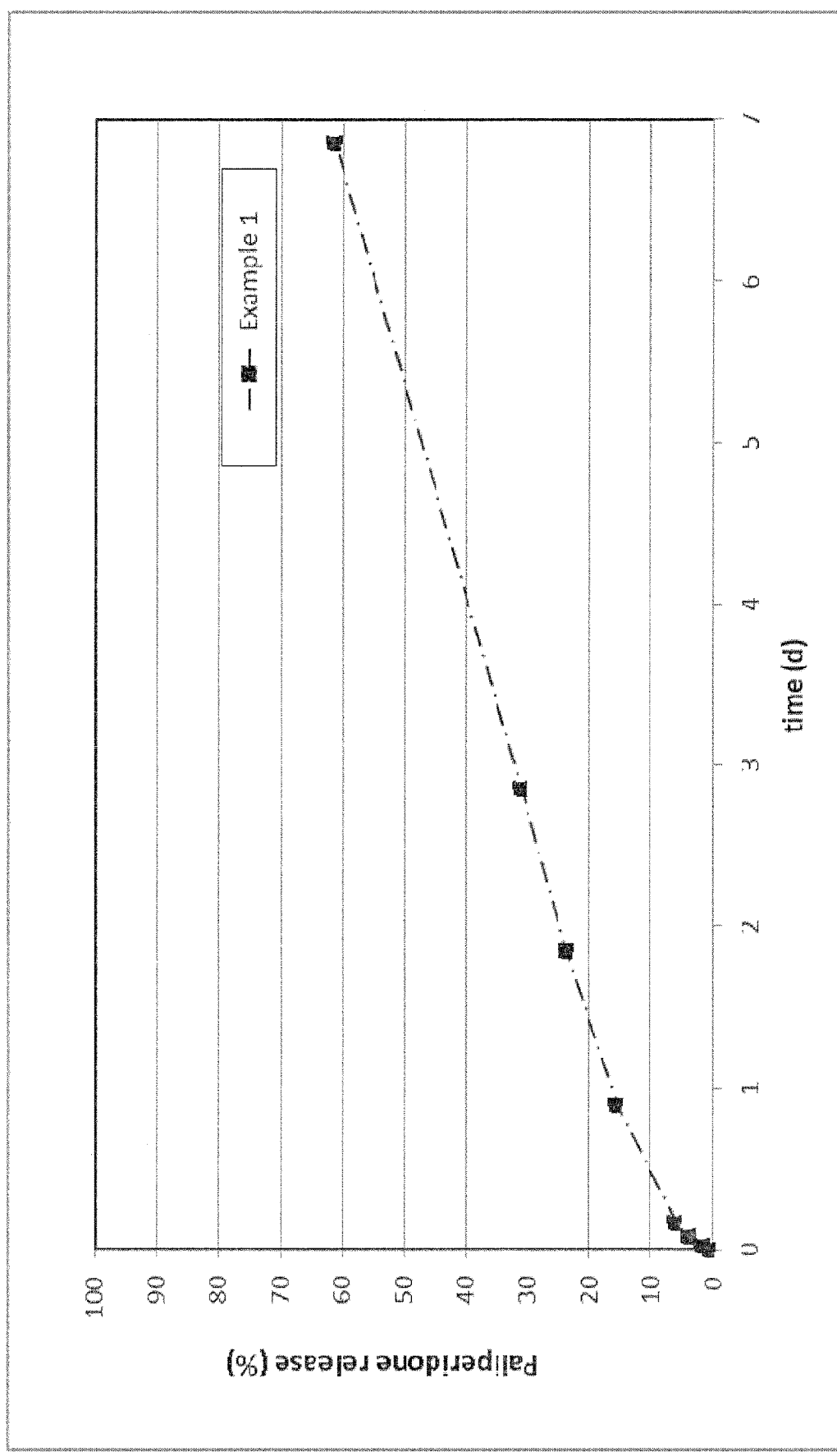
FIGS. 1 to 7 exhibit the in-vitro release profile of paliperidone loaded nano- and microparticles prepared in examples 1 to 7.
Figure 2:
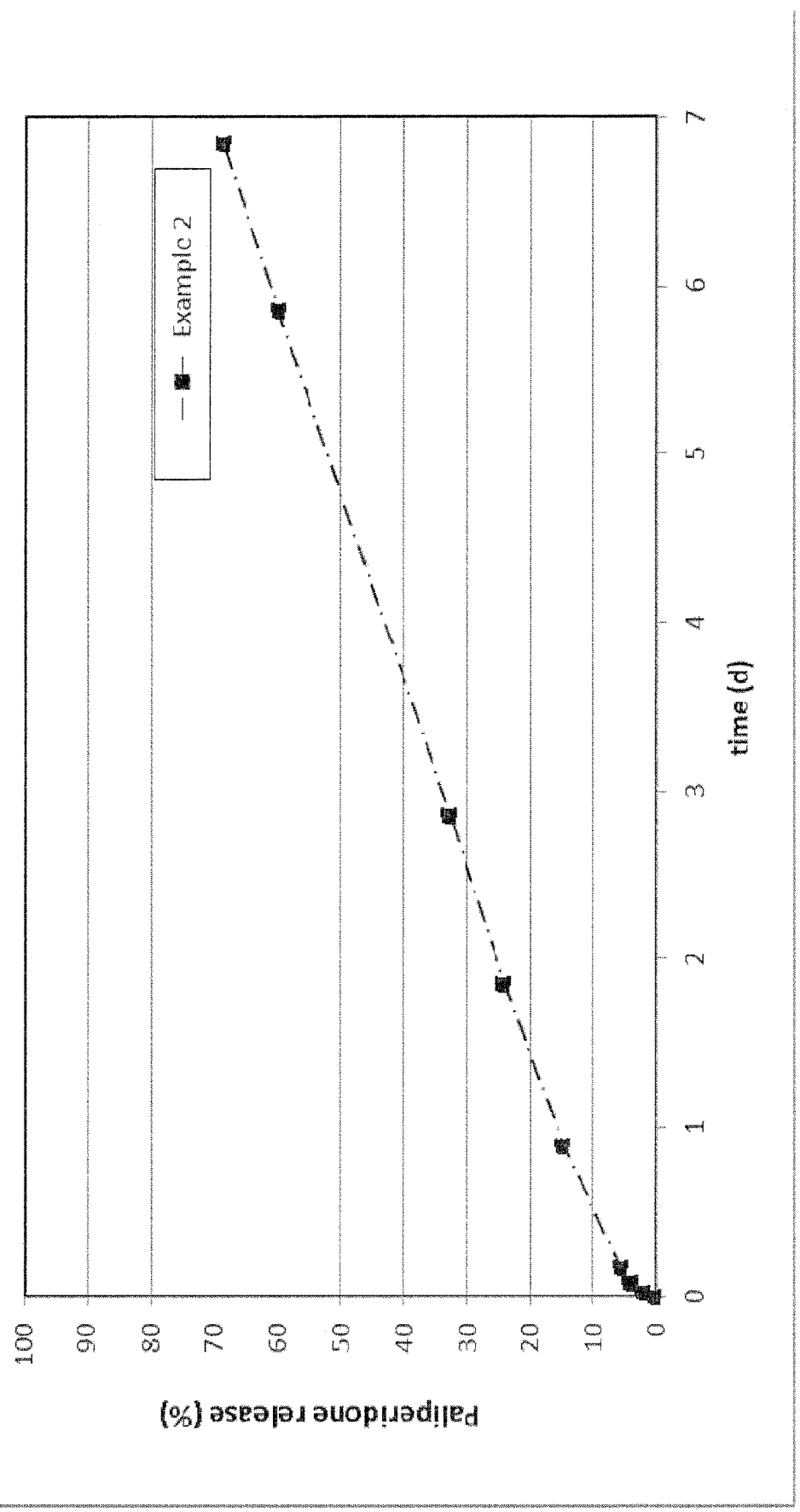
Figure 3:
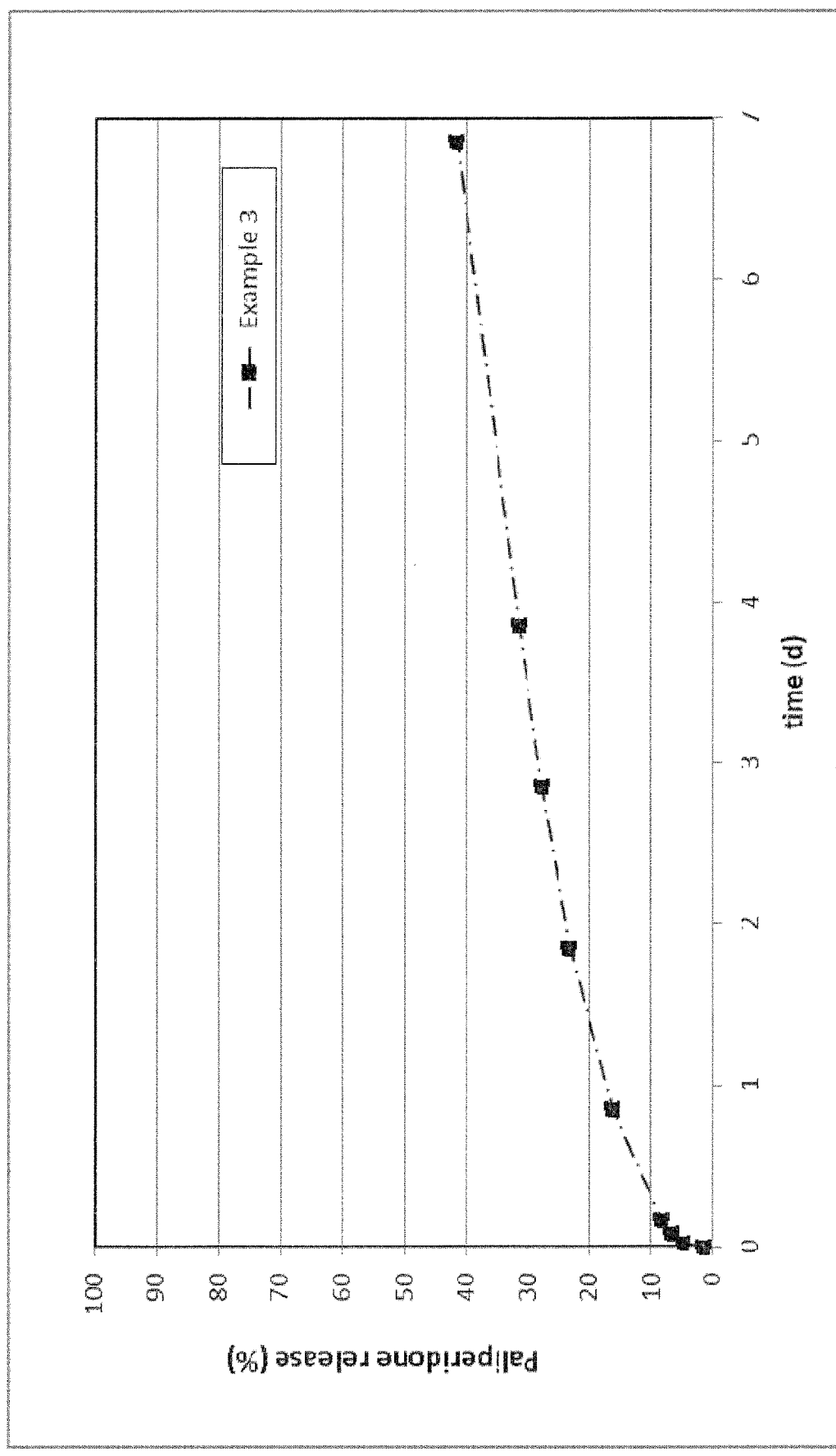
Figure 4:
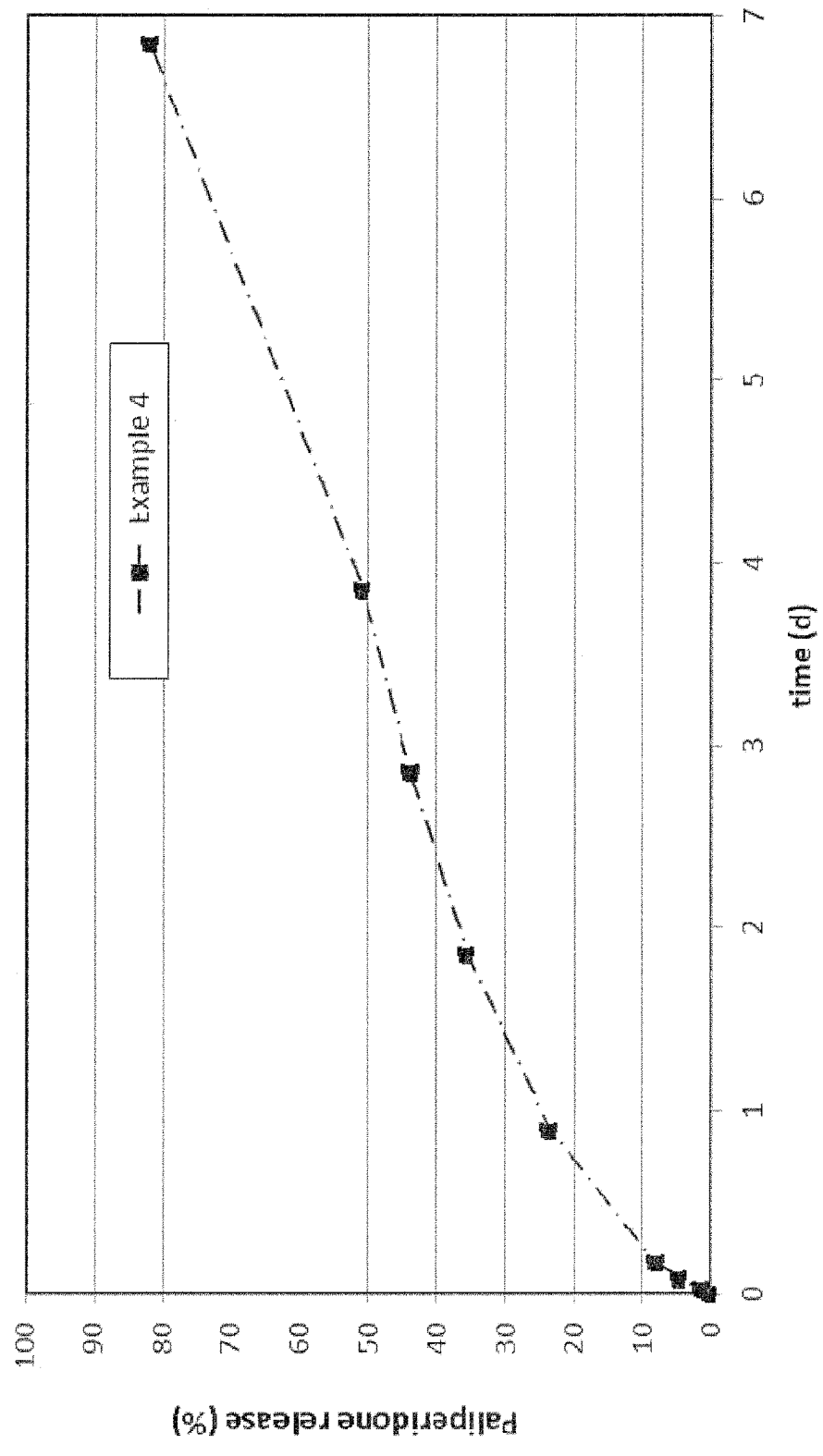
Figure 5:
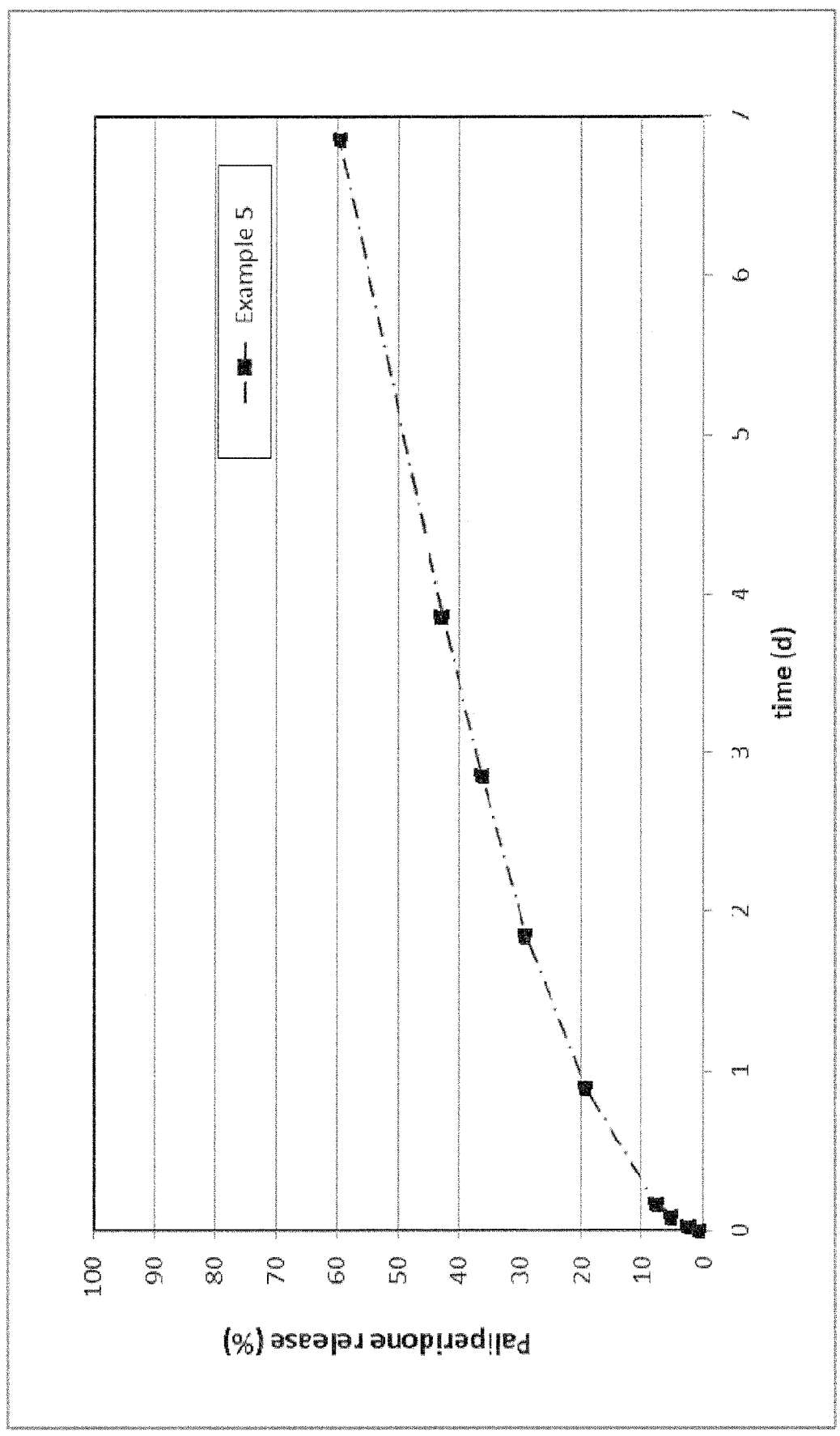
Figure 6:
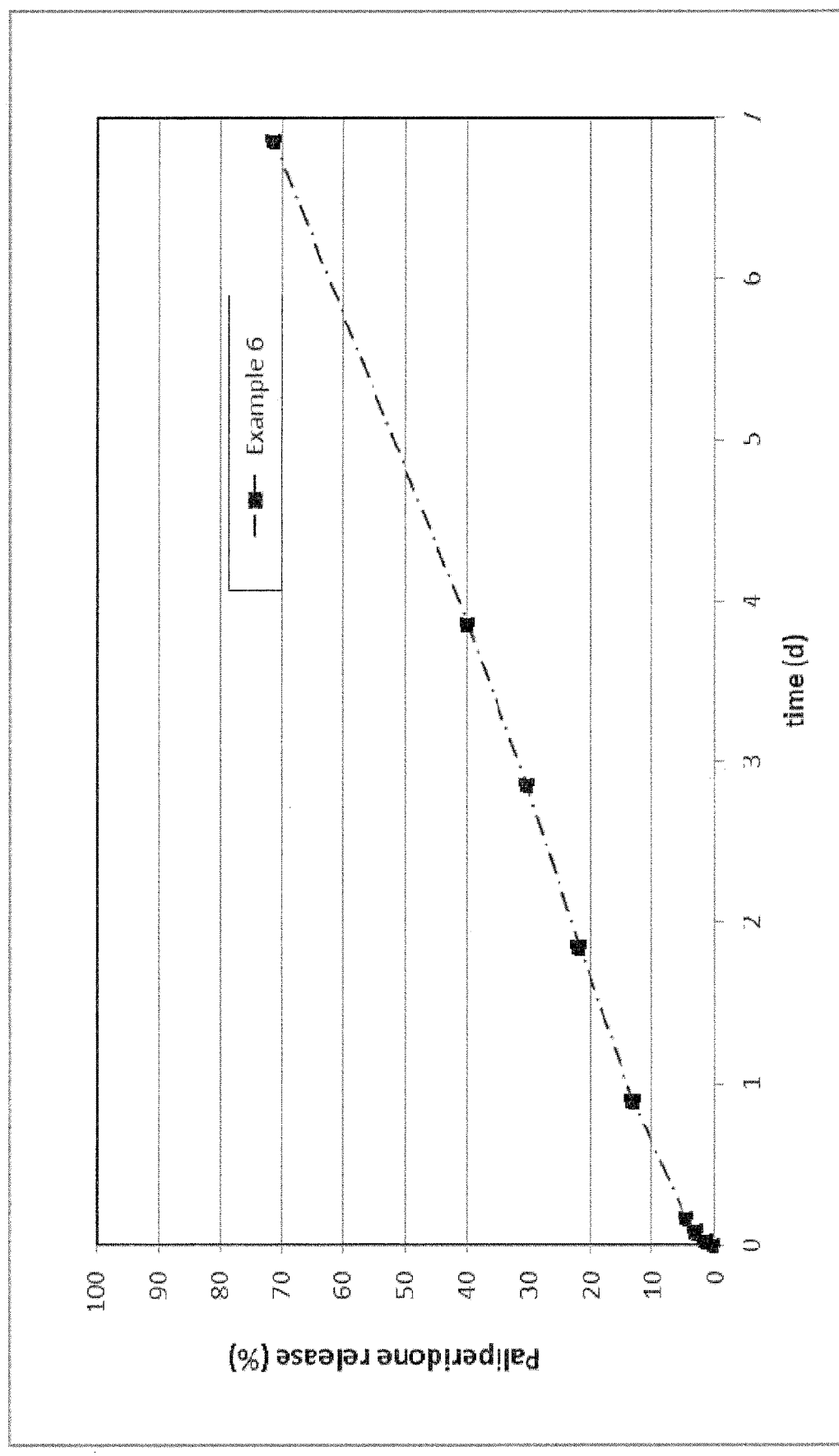
Figure 7:
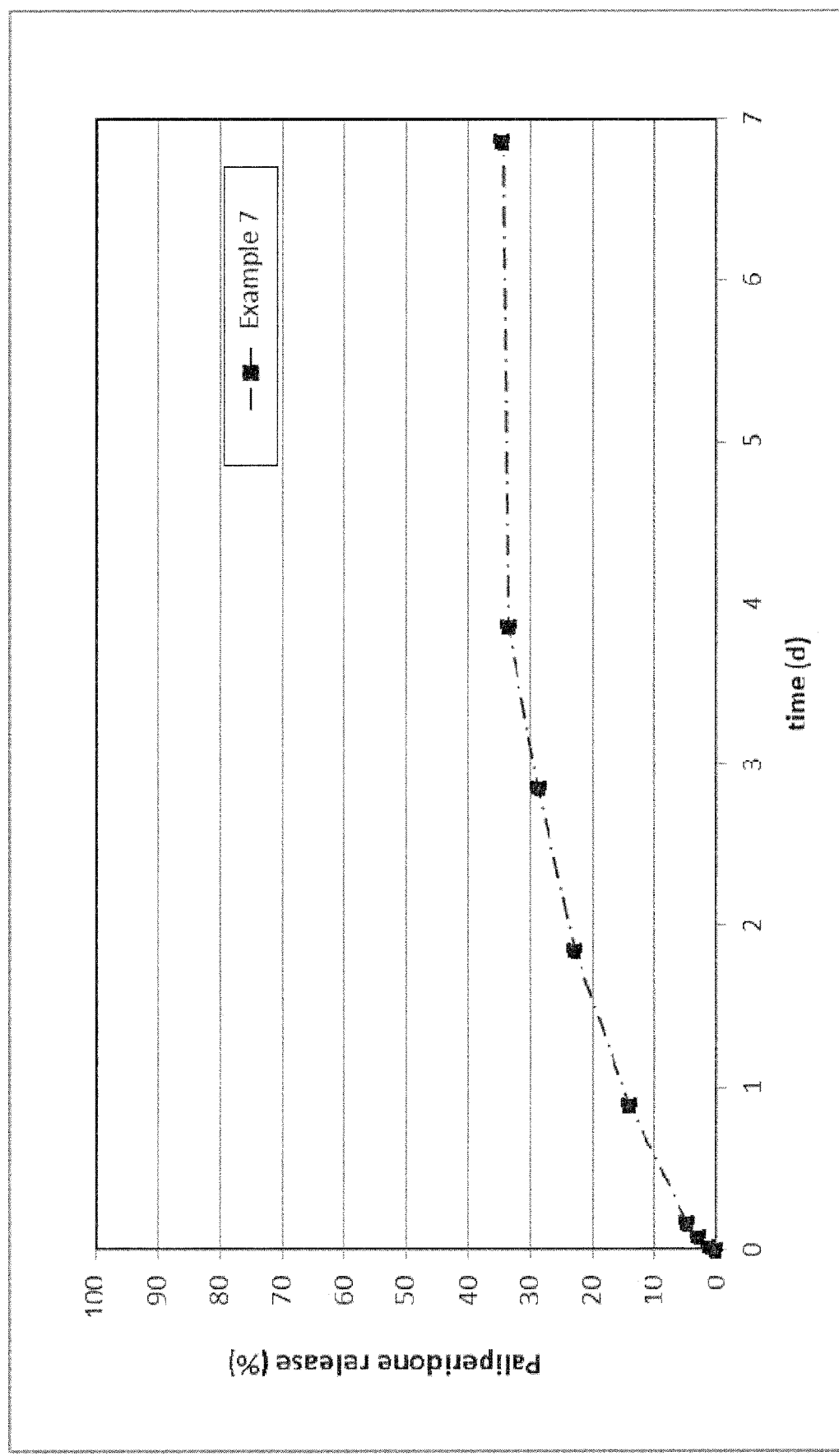
Figure 8:
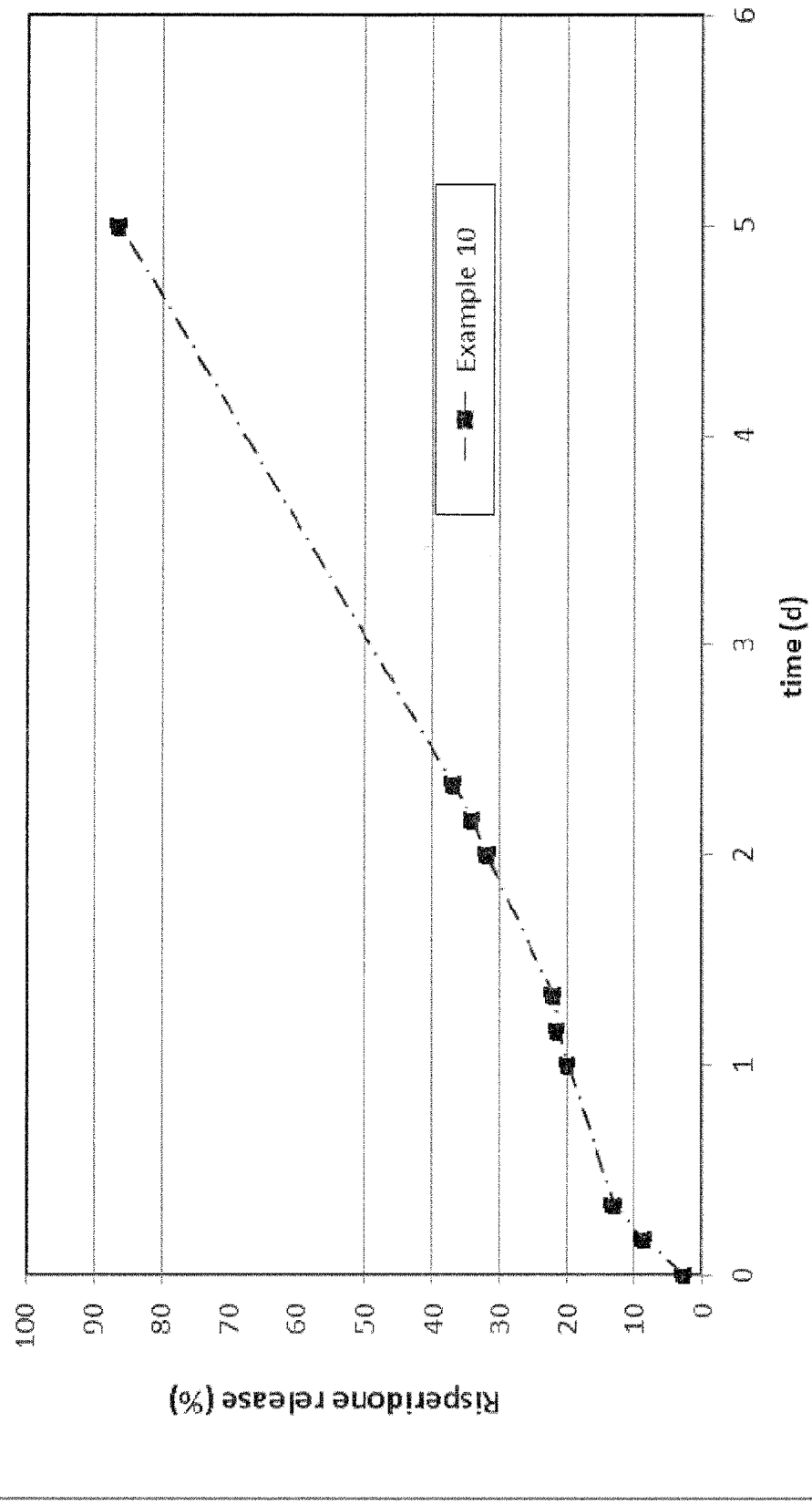
FIGS. 8 and 9 exhibit the in-vitro release profiles of risperidone loaded nano- and microparticles prepared in examples 10 to 11.
Figure 9:
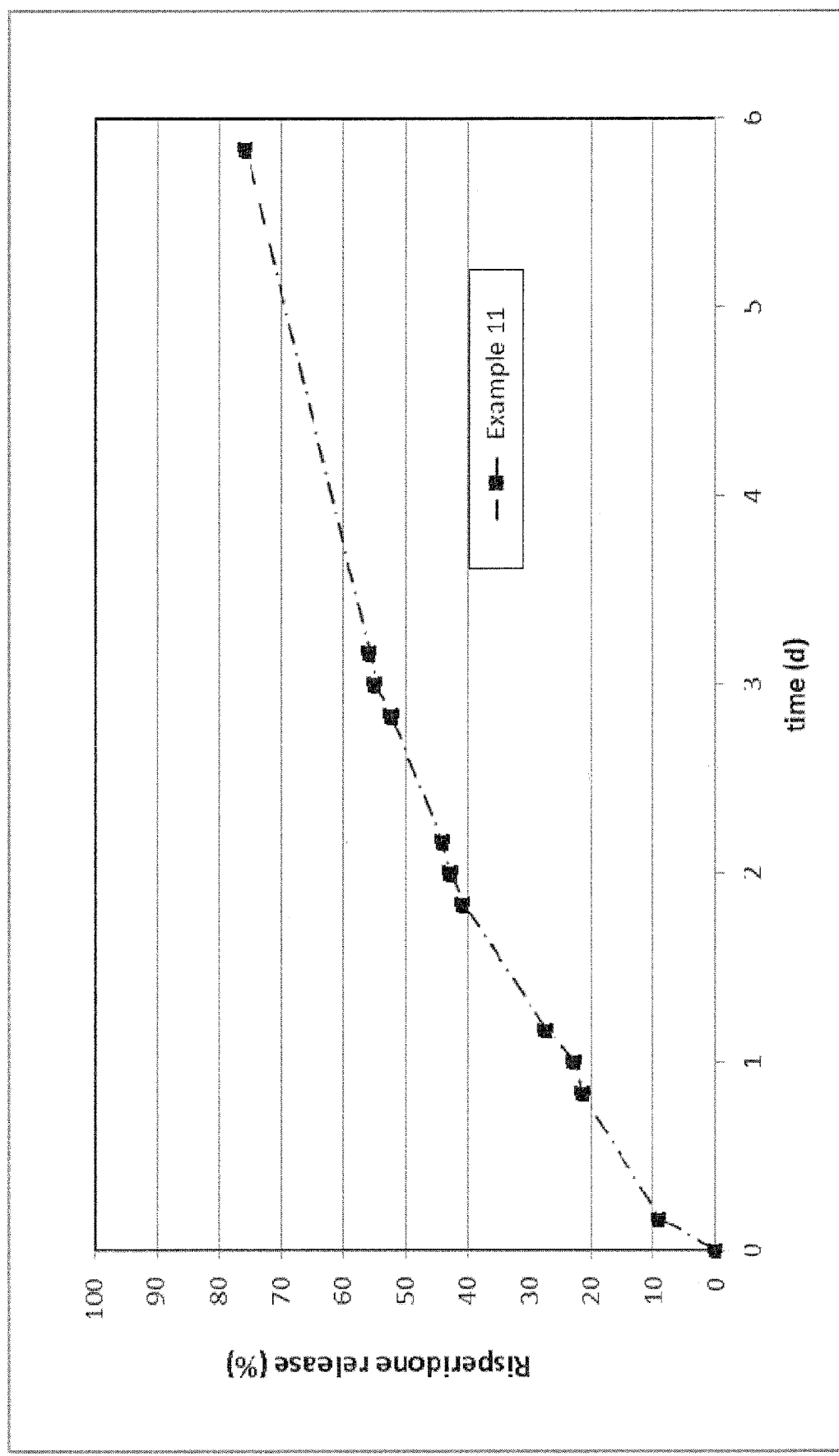

The invention claimed is:

1. A process for the production of nano- and/or microparticles containing a therapeutically active agent embedded in a polymer matrix or encapsulated by a polymer shell, said process comprising the steps of:

a) providing a solution of a polymer selected from polylactide, polyglycolide, and polyester copolymers comprising copolymerized units of lactic acid and/or glycolic acid in an organic solvent S1 having a solubility in water of 10 to 600 g/L;

b) providing a solution or suspension of a therapeutically active agent in an organic solvent or mixture of organic solvents S2 comprising at least 50 vol. % benzyl alcohol, c) combining the solutions or the solution and the suspension provided in step a) and step b) to provide an organic phase which comprises dissolved polymer and dissolved or dispersed therapeutically active agent in a mixture of the organic solvents S1 and S2;

d) agitating the organic phase provided in step c) in a vessel and adding an aqueous surfactant solution to the organic phase agitated in the vessel in a volume ratio of at least 2:1 in terms of the total volume of the aqueous surfactant solution to the total volume of the organic phase as provided in step c), thus causing the formation of a dispersion containing a continuous aqueous phase and a discontinuous organic phase; and e) allowing the spontaneous formation of a suspension of the nano- and/or microparticles via transfer of organic solvent from the discontinuous organic phase into the continuous aqueous phase directly after the dispersion has been formed in step d).

2. The process of claim 1, wherein the therapeutically active agent is a therapeutically active agent suitable to treat or prevent a mental disorder, including a neuropsychiatric disorder, cancer, an overactive bladder, or a postmenopausal disorder.

3. The process of claim 1, wherein the therapeutically active agent is selected from the group consisting of risperidone, paliperidone, aripiprazole, iloperidone, rivastigmine, duloxetine, donepezil, memantine, pramipexole, haloperidol, raloxifene, naltrexone and oxybutynine or from pharmaceutically acceptable salts of any of these therapeutic agents.

4. The process of claim 1, wherein the therapeutically active agent is contained in the nano- and/or microparticles in an amount of 15 wt. % or more, or 20 wt. % or more, based on the total weight of the nano- and/or microparticles.

5. The process of claim 1, wherein the therapeutically active agent is dispersed as an amorphous or crystalline solid in a polymer matrix.

6. The process of claim 1, wherein the polymer matrix or polymer shell of the prepared particles comprises a polymer selected from the group consisting of a polyglycolide homopolymer, a polylactide homopolymer, a copolymer of glycolide and lactide, a copolymer of glycolide and tetramethylglycolide, a copolymer of glycolide and δ-valerolactone, a copolymer of glycolide and ε-caprolactone, a copolymer of glycolide and trimethylene carbonate, a copolymer of lactide and tetramethylglycolide, a copolymer of lactide and δ-valerolactone, a copolymer of lactide and ε-caprolactone, a copolymer of lactide and trimethylene carbonate, a copolymer of glycolide and ethylene glycol, and a copolymer of lactide and ethylene gylcol.

7. The process of claim 6, wherein the polymer matrix or polymer shell of the prepared particles comprises a copolymer of glycolide and lactide.

8. The process of claim 1, wherein the solvent S2 is benzyl alcohol.

9. The process of claim 1, wherein the solubility of the solvent S1 in water is 20 to 400 g/L.

10. The process of claim 1, wherein the solvent S1 is selected from alkyl acetates, alkyl formates, methyl ethyl ketone, and mixtures of two or more thereof.

11. The process of claim 10, wherein the solvent S1 is selected from ethyl acetate, methyl acetate, ethyl formate, propyl formate, isopropyl formate, methyl ethyl ketone and mixtures of two or more thereof.

12. The process of claim 1, wherein the ratio of solvent or mixture of organic solvents S2 to solvent S1 in the organic phase provided in step c) of the process of the invention is 5-50 vol. % S2 to 50-95 vol. % S1, based on the sum of the volumes S1+S2 prior to their combination as 100 vol. %.

13. The process of claim 1, wherein the aqueous surfactant solution is added in step d) by adding the aqueous surfactant solution to the total volume of the organic phase under stirring.

14. The process of claim 1, wherein the addition of the aqueous surfactant solution takes place over a time period of 5 s to 5 min.

15. The process of claim 1, wherein steps c), d) and e) take place in the same vessel.

16. The process of claim 1, wherein the surfactant in the aqueous surfactant solution added in step d) is selected from polyvinyl alcohol, polyoxyethylene-polyoxypropylene-polyoxyethylene-triblock copolymers and fatty acid esters of polyoxyethylenesorbitan, or mixtures thereof.

17. A process for the preparation of a pharmaceutical formulation comprising a first step of preparing nano- and/or microparticles in accordance with the process of claim 1, and a subsequent step of forming a pharmaceutical formulation comprising the prepared nano- and/or microparticles.

18. The process of claim 17, wherein the pharmaceutical formulation is a depot formulation to be administered via the parenteral route.

19. The process of claim 18, wherein the nano- and/or microparticles contained in the formulation have a content of the therapeutically active agent of 15 wt. % or more.

* * * * *